(12) United States Patent
Otrando et al.

(10) Patent No.: US 10,080,562 B2
(45) Date of Patent: Sep. 25, 2018

(54) METHODS, SYSTEMS, AND DEVICES FOR SURGICAL SUTURING

(71) Applicant: Depuy Synthes Products, Inc., Raynham, MA (US)

(72) Inventors: Brian Otrando, Cumberland, RI (US); Kevin Zylka, Taunton, MA (US); Jonathan Bellas, Raynham, MA (US); James T. Spivey, Whitehouse Station, NJ (US); Peter Colby, Raynham, MA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 526 days.

(21) Appl. No.: 14/820,067

(22) Filed: Aug. 6, 2015

(65) Prior Publication Data
US 2017/0035415 A1    Feb. 9, 2017

(51) Int. Cl.
*A61B 17/04* (2006.01)
*A61B 17/062* (2006.01)
(Continued)

(52) U.S. Cl.
CPC ...... *A61B 17/0491* (2013.01); *A61B 17/0469* (2013.01); *A61B 17/0483* (2013.01); *A61B 17/062* (2013.01); *A61B 50/30* (2016.02); *A61B 2017/0023* (2013.01); *A61B 2017/0053* (2013.01); *A61B 2017/0479* (2013.01);
(Continued)

(58) Field of Classification Search
CPC . A61B 50/30; A61B 17/0469; A61B 17/0483; A61B 17/06114; A61B 17/062; A61B 17/06119; A61B 17/06133; A61B 2017/0053; A61B 2017/0479; A61B 2017/06142
See application file for complete search history.

(56) References Cited

U.S. PATENT DOCUMENTS

| 17,272 A | 5/1857 | Garvey |
| 527,263 A | 10/1894 | Blanchard |

(Continued)

FOREIGN PATENT DOCUMENTS

| DE | G 9214276.1 | 10/1992 |
| DE | 4235602 A1 | 4/1994 |

(Continued)

OTHER PUBLICATIONS

European Search Report and Written Opinion for EP App. No. 16182140.0 dated Jan. 3, 2017.
(Continued)

*Primary Examiner* — Christopher L Templeton
*Assistant Examiner* — Majid Jamialahmadi

(57) ABSTRACT

Various exemplary methods, systems, and devices for surgical suturing are provided. In general, a loading element can be configured to facilitate loading of a plate into a surgical instrument configured to facilitate passage of a suture through tissue. The surgical instrument can be configured to advance the suture through a tissue of a patient, to capture a free end or looped end of the suture after the suture's advancement through the tissue, and to pull the captured suture out of the patient's body with a portion of the suture remaining passed through the tissue within the patient's body.

13 Claims, 30 Drawing Sheets

(51) Int. Cl.
*A61B 90/00* (2016.01)
*A61B 17/00* (2006.01)
*A61B 50/30* (2016.01)
*A61B 17/06* (2006.01)

(52) U.S. Cl.
CPC .............. *A61B 2017/06095* (2013.01); *A61B 2090/0808* (2016.02); *A61B 2090/0811* (2016.02)

(56) References Cited

U.S. PATENT DOCUMENTS

| | | |
|---|---|---|
| 1,037,864 A | 9/1912 | Carlson et al. |
| 1,464,832 A | 6/1922 | Richardson |
| 1,449,087 A | 3/1923 | Bugbee |
| 1,500,884 A | 7/1924 | Murnin |
| 1,641,077 A | 8/1927 | Fouquet |
| 1,822,330 A | 9/1931 | Ainslie |
| 2,303,956 A | 12/1942 | Rossbacher |
| 2,738,790 A | 3/1956 | Todt et al. |
| 2,748,773 A | 6/1956 | Vacheresse |
| 2,948,222 A | 8/1960 | Pine |
| 3,090,386 A | 5/1963 | Curtis |
| 3,244,317 A | 4/1966 | Raybin |
| 3,349,772 A | 10/1967 | Rygg |
| 3,372,477 A | 3/1968 | Hoppe |
| 3,374,277 A | 3/1968 | Vandenberg |
| 3,393,687 A | 7/1968 | Whitman |
| 3,470,872 A | 10/1969 | Grieshaber |
| 3,470,875 A | 10/1969 | Johnson |
| 3,807,407 A | 4/1974 | Schweizer |
| 3,842,840 A | 10/1974 | Schweizer |
| 3,901,244 A | 8/1975 | Schweizer |
| 3,946,740 A | 3/1976 | Bassett |
| 4,164,225 A | 8/1979 | Johnson et al. |
| 4,345,601 A | 8/1982 | Fukuda |
| 4,587,202 A | 5/1986 | Borysko |
| 4,890,615 A | 1/1990 | Caspari et al. |
| 4,950,273 A | 8/1990 | Briggs |
| 4,957,498 A | 9/1990 | Caspari et al. |
| 4,981,149 A | 1/1991 | Yoon et al. |
| 5,059,201 A | 10/1991 | Asnis |
| 5,219,358 A | 6/1993 | Bendel et al. |
| 5,222,962 A | 6/1993 | Burkhart |
| 5,222,977 A | 6/1993 | Esser |
| 5,254,126 A | 10/1993 | Filipi et al. |
| 5,275,613 A | 1/1994 | Haber et al. |
| 5,281,237 A | 1/1994 | Gimpelson |
| 5,312,422 A | 5/1994 | Trott |
| 5,318,577 A | 6/1994 | Li |
| 5,364,409 A | 11/1994 | Kuwabara et al. |
| 5,387,221 A | 2/1995 | Bisgaard |
| 5,387,227 A | 2/1995 | Grice |
| 5,397,325 A | 3/1995 | Della Badia et al. |
| 5,403,328 A | 4/1995 | Shallman |
| 5,454,823 A | 10/1995 | Richardson et al. |
| 5,458,616 A | 10/1995 | Granger |
| 5,474,565 A | 12/1995 | Trott |
| 5,478,345 A | 12/1995 | Stone et al. |
| 5,480,406 A | 1/1996 | Nolan et al. |
| 5,499,991 A | 3/1996 | Garman et al. |
| D368,776 S | 4/1996 | Toy et al. |
| 5,522,820 A | 6/1996 | Caspari et al. |
| 5,540,704 A | 7/1996 | Gordon et al. |
| 5,562,686 A | 10/1996 | Sauer et al. |
| 5,571,090 A | 11/1996 | Sherts |
| 5,573,542 A | 11/1996 | Stevens |
| 5,613,977 A | 3/1997 | Weber et al. |
| 5,618,290 A | 4/1997 | Toy et al. |
| 5,632,751 A | 5/1997 | Piraka |
| 5,649,958 A | 7/1997 | Grimm et al. |
| 5,662,665 A | 9/1997 | Ludwick |
| 5,674,244 A | 10/1997 | Mathys |
| 5,676,675 A | 10/1997 | Grice |
| 5,690,652 A | 11/1997 | Wurster et al. |
| 5,690,653 A | 11/1997 | Richardson et al. |
| 5,704,925 A | 1/1998 | Otten et al. |
| 5,718,714 A | 2/1998 | Livneh |
| 5,728,107 A | 3/1998 | Zlock et al. |
| 5,728,113 A | 3/1998 | Sherts |
| 5,730,747 A | 3/1998 | Ek et al. |
| 5,749,879 A | 5/1998 | Middleman et al. |
| 5,797,927 A | 8/1998 | Yoon |
| 5,824,009 A | 10/1998 | Fukuda et al. |
| 5,833,697 A | 11/1998 | Ludwick |
| 5,843,125 A | 12/1998 | Jempolsky |
| 5,897,564 A * | 4/1999 | Schulze .......... A61B 17/0469 112/80.03 |
| 5,899,911 A | 5/1999 | Carter |
| 5,908,428 A | 6/1999 | Scirica et al. |
| 5,935,149 A | 8/1999 | Ek |
| 5,947,982 A | 9/1999 | Duran |
| 5,972,005 A | 10/1999 | Stalker et al. |
| 5,980,538 A | 11/1999 | Fuchs et al. |
| 5,993,466 A | 11/1999 | Yoon |
| 6,051,006 A | 4/2000 | Shluzas et al. |
| 6,074,403 A | 6/2000 | Nord |
| 6,113,610 A | 9/2000 | Poncet |
| 6,254,620 B1 | 7/2001 | Koh et al. |
| 6,371,963 B1 | 4/2002 | Nishtala et al. |
| 6,554,845 B1 | 4/2003 | Fleenor et al. |
| 6,723,107 B1 | 4/2004 | Skiba et al. |
| 6,770,084 B1 | 8/2004 | Bain et al. |
| 6,984,237 B2 | 1/2006 | Hatch et al. |
| D523,554 S | 6/2006 | Weisel |
| D529,173 S | 9/2006 | Weisel |
| 7,112,208 B2 | 9/2006 | Morris et al. |
| D530,421 S | 10/2006 | Topper et al. |
| 7,166,116 B2 | 1/2007 | Lizardi et al. |
| 7,318,802 B2 | 1/2008 | Suzuki et al. |
| 7,328,020 B2 | 2/2008 | Masuda et al. |
| 7,377,926 B2 | 5/2008 | Topper et al. |
| 7,381,212 B2 | 6/2008 | Topper et al. |
| 7,585,305 B2 | 9/2009 | Dreyfuss |
| 7,879,046 B2 | 2/2011 | Weinert et al. |
| 7,879,048 B2 | 2/2011 | Bain et al. |
| 8,057,489 B2 | 11/2011 | Stone et al. |
| 8,114,128 B2 | 2/2012 | Cauldwell et al. |
| 8,177,796 B2 | 5/2012 | Akyuz et al. |
| 8,540,732 B2 | 9/2013 | Weinert et al. |
| 2002/0065526 A1 | 5/2002 | Oren et al. |
| 2002/0103493 A1 | 8/2002 | Thal |
| 2002/0138084 A1 | 9/2002 | Weber |
| 2002/0165549 A1 | 11/2002 | Owusu-Akyaw et al. |
| 2003/0065337 A1 | 4/2003 | Topper et al. |
| 2003/0220658 A1 | 11/2003 | Hatch et al. |
| 2003/0233106 A1 | 12/2003 | Dreyfuss |
| 2004/0010273 A1 | 1/2004 | Diduch et al. |
| 2004/0015177 A1 | 1/2004 | Chu |
| 2004/0249394 A1 | 12/2004 | Morris et al. |
| 2006/0020274 A1 | 1/2006 | Ewers et al. |
| 2008/0300612 A1 | 12/2008 | Riza et al. |
| 2008/0312669 A1 | 12/2008 | Vries et al. |
| 2009/0076544 A1 | 3/2009 | DiMatteo et al. |
| 2009/0138029 A1 | 5/2009 | Saliman et al. |
| 2010/0121352 A1 | 5/2010 | Murray et al. |
| 2010/0256656 A1 | 10/2010 | Park |
| 2010/0331863 A2 | 12/2010 | Saliman et al. |
| 2011/0118760 A1 | 5/2011 | Gregoire et al. |
| 2011/0172675 A1* | 7/2011 | Danta .................. A61B 17/28 606/107 |
| 2012/0041457 A1 | 2/2012 | De Vries et al. |
| 2013/0226231 A1 | 8/2013 | Weinert et al. |
| 2014/0276987 A1 | 9/2014 | Saliman |
| 2015/0173742 A1 | 6/2015 | Palese et al. |

FOREIGN PATENT DOCUMENTS

| | | |
|---|---|---|
| EP | 0778004 A1 | 6/1997 |
| EP | 0778004 B1 | 3/2003 |
| EP | 1961390 A1 | 8/2008 |
| JP | 1083252 | 3/1989 |
| JP | 7328020 | 12/1995 |
| WO | WO-199727807 A1 | 8/1997 |

(56) References Cited

FOREIGN PATENT DOCUMENTS

| WO | WO-200156478 A1 | 8/2001 |
| WO | WO-2005107606 A1 | 11/2005 |
| WO | WO-2007033314 A2 | 3/2007 |

OTHER PUBLICATIONS

Duerig et al., "An Overview of Nitinol Medical Applications," Materials Science and Engineering A273-275. 149-160 (1999).
"Endoscopy 2009 Product Catalog," Smith & Nephew. 1-311 (2009).
"ExpresSew Surgical Technique," DePuy Mitek. 1-2 (2005).
"ExpresSewII Surgical Technique," DePuy Mitek. 1-8 (2007).
"ExpresSewIII Flexible Suture Passer: Surgical Technique Guide," DePuy Mitek. 1-8 (2011).
"First Pass Suture Passer," ArthroCare Sports Medicine. 1-5 (2010).
Kuiper, Scott, "BiPass Suture Punch: Surgical Protocol by Scott Kuiper, M.D. Biomet Sports Medicine." 1-8 (2008).
"Scorpion: Fulfilling the Need for Precision and Speed in Arthroscopic Rotator Cuff and Labral Repair," Arthrex, Inc. 1-8 (2012).

\* cited by examiner

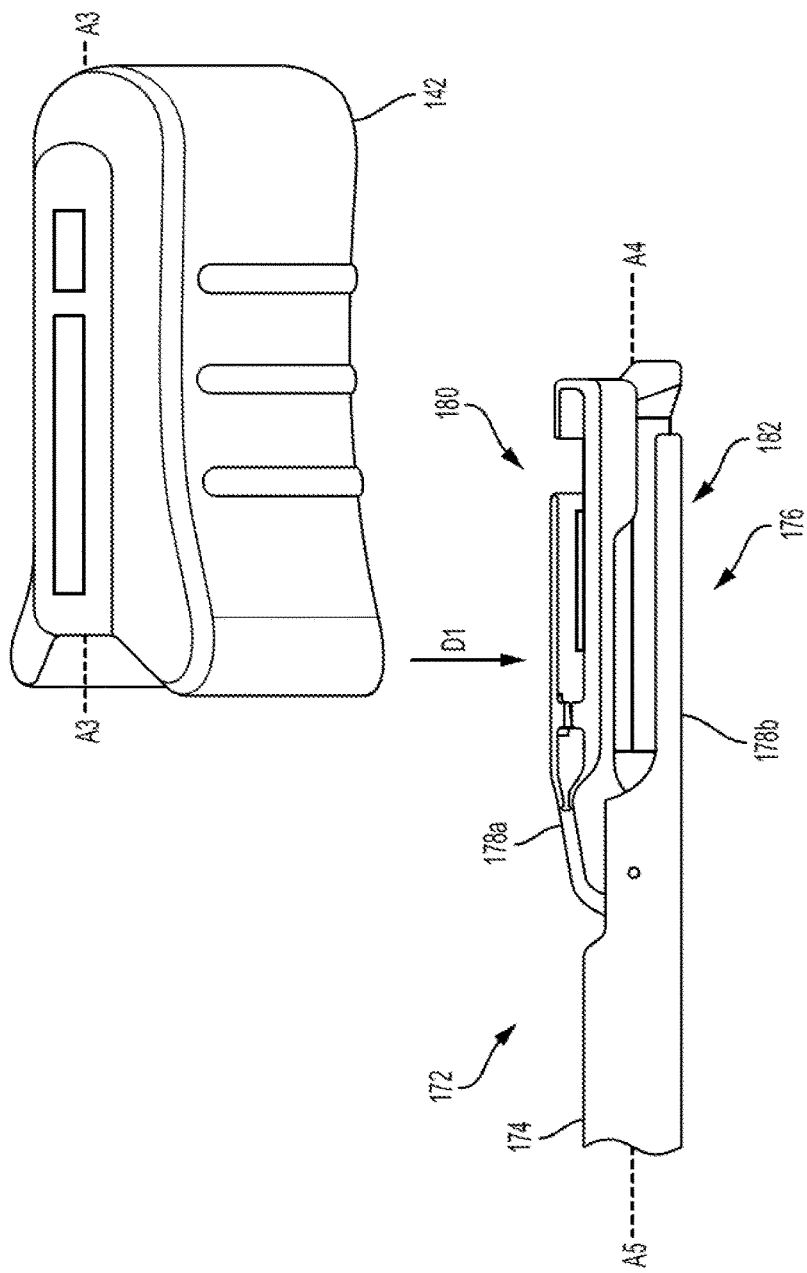

METHODS, SYSTEMS, AND DEVICES FOR SURGICAL SUTURING

FIELD

The present disclosure relates generally to methods, systems, and devices for surgical suturing.

BACKGROUND

Suturing apparatus in the past have been required to have an elongate configuration and a low profile facilitating their use through cannulas in less invasive surgery. These devices have typically included opposing jaws which clamp on to the tissue to be sutured. Beyond this simple clamping motion, typically facilitated by scissor handles, the mechanism for threading a suture between the jaws and through the tissues have been exceedingly complex.

This complexity has derived primarily from the fact that the elongated, low profile configuration calls for an operating force that can be transmitted through an elongate tube. This force along the axis of the instrument must then be converted into a force extending generally perpendicular to the axis between the jaws. No simple structure has been devised to accommodate this transition. Furthermore, loading a suture onto a mechanism has also been complicated due to the complexity of the suturing mechanisms.

Accordingly, there remains a need for improved methods, systems, and devices for surgical suturing.

SUMMARY

In general, methods, systems, and devices for surgical suturing are provided.

In one aspect, a surgical system is provided that in one embodiment includes an outer member and an inner member. The outer member has an internal cavity therein and has proximal and distal ends. The proximal end of the outer member has an opening therein that is in communication with the internal cavity. The inner member has proximal and distal ends and is an independent element from the outer member. The distal end of the inner member is configured to be inserted through the opening of the outer member and into the internal cavity of the outer member. The inner member includes a seat configured to removably and replaceably receive a plate therein. The proximal end of the inner member has a bore formed therein. The bore is configured to receive therein a distal end of a surgical instrument. The inner and outer members are configured to cause the plate to advance into the bore from the seat in response to the inner member being inserted into the internal cavity.

The surgical system can have any number of variations. For example, the system can include a plate configured to removably and replaceably be received in the seat. The plate can be configured to facilitate passage of a suture through tissue. For another example, the outer member can have an internal protrusion that extends into the internal cavity. The internal protrusion can be configured to push the plate into the bore from the seat. For yet another example, the inner member can have a single position relative to the outer member in which the inner member is configured to be inserted through the opening of the outer member and into the internal cavity of the outer member. For still another example, the inner member can have a slot formed in an external surface thereof. The slot can have an open proximal end and a closed distal end. For another example, the inner member can include a stop element configured to stop movement of the inner member in the distal direction within the internal cavity once the inner member has advanced a predetermined amount into the internal cavity. For yet another example, in response to the plate being fully advanced into the bore from the seat, at least one of the inner and outer members can be configured to generate at least one of an audible confirmation and a tactile confirmation of the full advancement.

For another example, the inner and outer members can have corresponding engagement members configured to orient the inner and outer members relative to one another in a predetermined orientation. The engagement member of one of the inner and outer members can include a slot, and the engagement member of the other of the inner and outer members can include a protrusion configured to slide within the slot during the advancement of the inner member in the distal direction into the internal cavity.

For yet another example, the inner member can have one or more ribs formed on a top surface thereof. The one or more ribs can be configured to at least one of prevent the inner member from backing out of the outer member in a proximal direction until a predetermined amount of force is applied to at least one of the inner and outer members, and limit movement of the inner member in the distal and proximal directions relative to the outer member until a predetermined amount of force is applied to at least one of the inner and outer members.

For still another example, the surgical system can include a surgical instrument having a distal end configured to be received within the bore of the inner member. The inner and outer members can be configured to cause the plate to advance from the seat into the distal end of the surgical instrument within the bore of the inner member. The distal end of the surgical instrument can include a pair of jaws configured to move between open and closed positions. The bore can be configured to receive the pair of jaws therein with the pair of jaws in the closed position. The distal end of the surgical instrument can be configured to be inserted into the bore of the inner member in a single predetermined orientation relative to the inner member.

In another aspect, a surgical method is provided that in one embodiment includes inserting the distal end of the surgical instrument into the bore of the inner member of the surgical system. The inserting is performed by a user, and the inserting causes the plate to advance into the bore from the seat such that the plate advances into the distal end of the surgical instrument. The method also includes removing from the bore the distal end of the surgical instrument having the plate advanced therein. The method can have any number of variations.

In another embodiment, a surgical system is provided that includes a surgical instrument, a plate, and a loading element. The surgical instrument includes at a distal end thereof first and second jaws configured to grasp tissue therebetween. The surgical instrument is configured to pass a suture through tissue. The plate is configured to facilitate the passage of the suture through the tissue. The loading element includes an outer housing and an inner housing that is configured to be seated at least partially within the outer housing. At least one of the inner and outer housings can be movable relative to the other. The inner housing can be configured to removably and replaceably seat the plate in a loading configuration. The inner housing can be configured to receive at least a portion of the first jaw therein. When the inner housing is seated at least partially within the outer housing, the plate is seated in the inner housing, and at least the portion of the first jaw is received in the inner housing, movement of the outer housing relative to the inner housing is configured to cause the plate to move into the first jaw in a loaded configuration.

The surgical system can vary in any number of ways. For example, the first and second jaws can be configured to move between open and closed positions. At least the portion of the first jaw can be configured to be received in the inner housing when the first and second jaws are in the closed position. For another example, the surgical instrument can include an elongate shaft having the first and second jaws at a distal end thereof. The elongate shaft can define a first longitudinal axis. The inner housing can have a bore formed therein that defines a second longitudinal axis. The bore can be configured to receive at least the portion of the first jaw therein with the first and second longitudinal axes being substantially parallel to one another.

In another aspect, a surgical method is provided that includes inserting a distal end of a surgical instrument into a bore formed in a proximal end of an inner housing of a loading element. The inner housing is removably and replaceably seating a plate. The surgical instrument is configured to pass a suture through tissue. The method also includes moving at least one of the inner housing and an outer housing of the loading element relative to the other, thereby causing the plate to move from being seated in the inner housing to being seated in the distal end of the surgical instrument.

The method can vary in any number of ways. For example, the distal end of the surgical instrument can include a pair of jaws configured to move between open and closed positions. The pair of jaws in the closed position can define a first longitudinal axis, the bore of the inner housing can define a second longitudinal axis, and the distal end of the surgical instrument can be inserted into the bore with the first and second longitudinal axes being substantially parallel to one another. Inserting the distal end of the surgical instrument into the bore can include inserting the pair of jaws in the closed position into the bore.

For another example, the surgical instrument can include an elongate shaft extending distally from a proximal handle of the surgical instrument. The elongate shaft can define a first longitudinal axis, the bore of the inner housing can define a second longitudinal axis, and the distal end of the surgical instrument can be inserted into the bore with the first and second longitudinal axes being substantially parallel to one another.

For still another example, the method can include engaging the tissue with the distal end of the surgical instrument, and actuating the surgical instrument so as to cause the surgical instrument to pass the suture through the engaged tissue, thereby causing deflection of the plate seated in the distal end of the surgical instrument.

In another embodiment, a surgical method is provided that includes seating a loading element having a plate seated therein onto a distal end of a surgical instrument by advancing the loading element in a first direction relative to the distal end of the surgical instrument. The surgical instrument is configured to pass a suture through tissue. The method also includes advancing in a second direction the loading element seated on the distal end of the surgical instrument, thereby causing the plate to move from a seated condition in the loading element to a seated condition in the distal end of the surgical instrument. The second direction is substantially perpendicular to the first direction. The method also includes removing the loading element from the surgical instrument, the plate remaining seated in the distal end of the surgical instrument.

The method can have any number of variations. For example, the second direction can be a direction toward a handle at a proximal end of the surgical instrument. For another example, the distal end of the surgical instrument can include a pair of jaws, and the plate being seated in the distal end of the surgical instrument can include the plate being seated in one of the jaws. The method can also include grasping tissue with the pair of jaws, and actuating the surgical instrument so as to cause the surgical instrument to pass the suture through the grasped tissue, thereby causing deflection of the plate seated in the surgical instrument.

BRIEF DESCRIPTION OF DRAWINGS

This invention will be more fully understood from the following detailed description taken in conjunction with the accompanying drawings, in which:

FIG. 24 is a perspective view of the loading element of FIG. 20 and of a distal portion of another embodiment of a surgical instrument configured to pass a suture through tissue;

DETAILED DESCRIPTION

Figure 1:
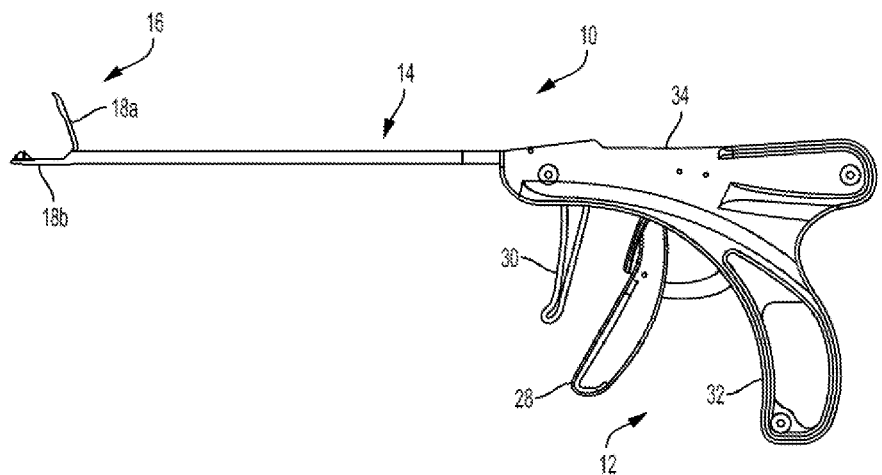
FIG. 1 is a side schematic view of one embodiment of a surgical instrument configured to pass a suture through tissue.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods, systems, and devices for surgical suturing are provided. In general, a loading element (also referred to herein as a "loader") can be configured to facilitate loading of a plate (also referred to herein as a "retainer plate") into a surgical instrument configured to pass a suture through tissue. The surgical instrument can be configured to advance the suture through tissue of a patient, to capture a free end or looped end of the suture after the suture's advancement through the tissue, and to pull the captured suture out of the patient's body with a portion of the suture remaining passed through the tissue within the patient's body. The suture can be passed through a variety of tissues, and the suture's passage may be useful in a variety of surgical procedures, as will be appreciated by a person skilled in the art. For example, the suture can be passed through a rotator cuff tissue in a rotator cuff repair procedure.

Although the surgical instrument may securely capture the suture after the suture's passage through tissue, in some instances, the surgical instrument's grasp of the suture may not be as secure as in other instances due to any one or more factors such as size of the suture, material forming the suture, anatomy of the patient, lack of user experience, and size of the tissue. Pulling the suture out of the patient's body may thus be difficult since the suture may be slip fully out of the surgical instrument's grip and/or become less tightly held by the surgical instrument during the pull-out process. The suture slipping fully out of the surgical instrument's grasp may require re-capturing the suture within the patient's body, which can be cumbersome and/or time-consuming. The suture becoming less tightly held by the surgical instrument while the captured suture is being pulled out of the patient's body may require a user manipulating the surgical instrument to apply an increased force to pull out the suture, which may be difficult given the user's strength and/or surgical space constraints, and/or may require the suture to be pulled out of the patient's body at an awkward angle. Even when the suture is securely captured by the surgical instrument after the suture's passage through tissue, the suture may slip fully out of the surgical instrument's grip (e.g., due to the pulling force) while the captured suture is being pulled out of the patient's body such that the suture must be re-captured within the patient's body, and/or the suture may become less tightly held by the surgical instrument while the captured suture is being pulled out of the patient's body such that a user manipulating the surgical instrument must apply an increased force to pull out the suture.

The plate loaded into the surgical instrument can be configured to facilitate manipulation of the suture. In particular, the plate can be configured to facilitate the instrument's capture of a suture after the suture has been passed through the tissue, which may facilitate secure pulling of the suture out of the patient's body. The plate can be configured to be loaded into an end effector at a distal end of the surgical instrument. The end effector can be configured to capture the suture after the suture has been passed through the tissue. The plate can be configured to facilitate the end effector's grasp of the captured suture, e.g., strengthen the instrument's grasp of the suture, and thereby help prevent the suture from fully slipping out of the end effector and help prevent the suture from becoming less securely held by the end effector after the suture's capture by the end effector.

It may be difficult to load the plate into the surgical instrument, e.g., into the instrument's end effector, for one or more reasons. For example, the plate can be a relatively small element that may be difficult for a user to manipulate by hand and load into the instrument. For another example, the plate can be configured to deform in shape in response to the instrument's capturing of the suture, but this deformability may allow the plate to deform during its loading into the instrument. The plate being loaded into the instrument in a deformed state may reduce the plate's effectiveness in helping the instrument to hold onto the captured suture. For yet another example, it may be difficult for a user to recognize whether or not the plate is properly loaded into the instrument, e.g., because it may be difficult to visually observe the plate within the end effector, because the user is inexperienced, etc. Improper loading of the plate into the instrument may reduce, if not entirely eliminate, the plate effectiveness in facilitating the instrument's grasp of the suture.

The loading element can be configured to facilitate loading of the plate into the instrument, e.g., into the end effector of the instrument, and thereby help make the plate less difficult to load into the instrument. In other words, the loading element may make the plate easier to load into the instrument regardless of the plate's size, may prevent the plate from deforming during its loading into the instrument, and/or may be configured to facilitate confirmation of the plate's proper loading into the instrument. The loading element can have a variety of sizes, shapes, and configurations, as discussed further below.

Figure 2:
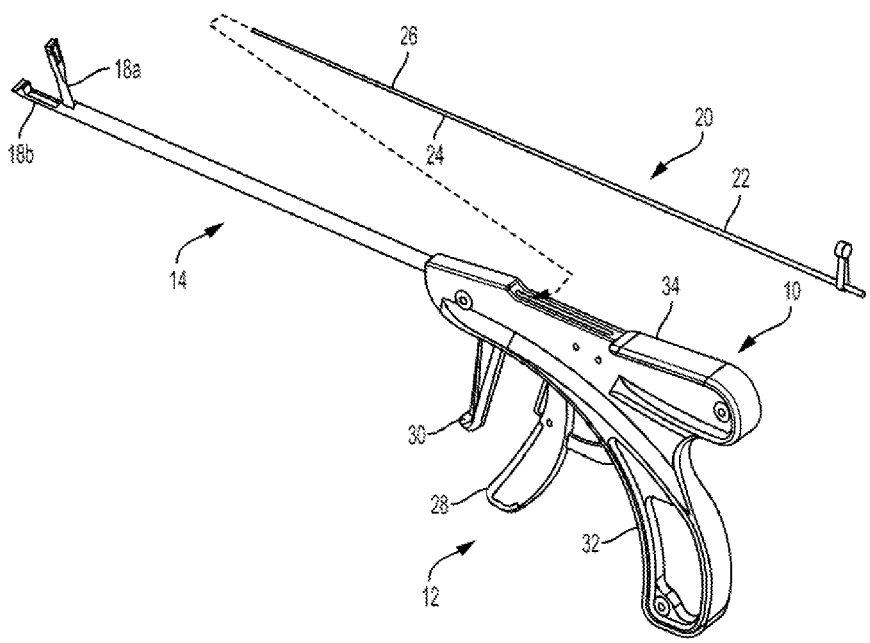
FIG. 2 is a perspective view of the surgical instrument of FIG. 1 and one embodiment of a needle loadable therein.

FIGS. 1 and 2 illustrate one embodiment of a surgical instrument 10 configured to facilitate passage of a suture through tissue. As in this illustrated embodiment, the instrument 10 can include a proximal handle portion 12, an elongate shaft 14 extending distally from the handle portion 12, and an end effector 16 coupled to a distal end of the shaft 14. The end effector 16 can include a first or upper jaw 18a and a second or lower jaw 18b configured to grasp tissue therebetween. The first jaw 18a is configured to move relative to the lower jaw 18b and the shaft 14 to facilitate the tissue grasping. In other embodiments, as will be appreciated by a person skilled in the art, the lower jaw 18b can be configured to move relative to the upper jaw 18a and the shaft 14, or both of the upper and lower jaws 18a, 18b can be configured to move relative to the shaft 14.

The instrument 10 can be configured to have a needle 20 removably and replaceably seated therein. As shown in this illustrated embodiment, the needle 20 can include a proximal needle body 22 that has a slotted distal end 24 and a flat bendable extension 26 that is within and is welded to the slotted distal end 24 of the needle body 22. The needle 20 can be configured to move relative to the shaft 14 and the end effector 16 to facilitate passage of a suture (not shown) through tissue. Various embodiments of using a needle loaded into a surgical instrument to facilitate passage of a suture through tissue are further described in U.S. Pat. No. 8,540,732 entitled "Suturing Apparatus And Method" filed Dec. 17, 2010, which is hereby incorporated by reference in its entirety.

The handle portion 12 can have a variety of configurations. As shown in this illustrated embodiment, the handle portion 12 can include a jaw closure trigger 28, a needle movement trigger 30, a stationary handle 32, and a housing 34. The stationary handle 32 can be part of the housing 34, as shown. The jaw closure trigger 28 can be configured to move relative to the stationary handle 32 to open and close the end effector 16 (e.g., to move the upper jaw 18a of the end effector 16 relative to the lower jaw 18b). The needle movement trigger 30 can be configured to move the needle 20 relative to the shaft 14 and the end effector 16. The housing 34 can house various components therein configured to facilitate the opening and closing of the end effector 16 and/or to facilitate the movement of the needle 20. The handle portion 12 is generally configured and usable similar to handle portions of surgical instruments described in previously mentioned U.S. Pat. No. 8,540,732 entitled "Suturing Apparatus And Method" filed Dec. 17, 2010.

The instrument 10 is generally configured and usable similar to surgical instruments configured to facilitate passage of a suture through tissue using a needle that are described in previously mentioned U.S. Pat. No. 8,540,732 entitled "Suturing Apparatus And Method" filed Dec. 17, 2010. In the illustrated embodiment of FIGS. 1 and 2, however, the end effector 16 is configured to seat a retainer plate (not shown) therein. Namely, the upper jaw 18a is configured to seat a retainer plate therein. The upper jaw 18a can have a variety of configurations.

In general, the upper jaw 18a can be configured to removably and replaceably seat the retainer plate therein. The plate may thus be removed from the instrument 10 and replaced after its use in a surgical procedure, e.g., after being used in connection with capturing a suture. The plate may become deformed during its use, as discussed further below, so as to reduce its effectiveness in any subsequent use to capture a suture. Thus, replacement of the plate may allow the instrument 10 to be re-used with other plates in the same surgical procedure and/or in subsequent surgical procedures. If the instrument 10 is reconditioned after its use for reuse in another surgical procedure, it may be difficult for the plate and/or parts of the instrument 10 near the plate seated therein to be fully cleaned after use of the plate and the instrument. The removability of the plate may facilitate proper reconditioning of the instrument 10 since the used plate may be removed prior to the reconditioning.

A surgical instrument such as the instrument 10 can be provided as part of a kit that includes a plurality of retainer plates each configured to be removably and replaceably loaded into the instrument. The kit may make it easier to use multiple plates during the course of a single surgical procedure by making the plates easily accessible. Each of the plates included in the kit can be the same as one another or any one or more of the plates can differ from any one or more of the other plates. The plates being the same as one another may provide predictability to a user (e.g., a surgeon) and/or may speed plate loading since no choice need be made between the identical ones of the plates. The plates not all being the same as one anther may allow the user to choose a particular type of plate that the user may prefer in general and/or for the particular surgical procedure to be performed. Different types of plates are discussed further below. The kit can also include a single needle (e.g., the needle 20) or can include a plurality of needles, which may or may not include the illustrated needle 20. Similar to that discussed above regarding the kit including multiple plates, the multiple needles included in the kit can all be the same as one another, or any one or more of the needles can differ from any one or more of the other needles. The kit can also include a loading element. While the kit may include multiple loading elements, only a single loading element is needed in the kit since the loading element can be configured to be reused to sequentially load plates into the instrument, as discussed further below.

Figure 3:
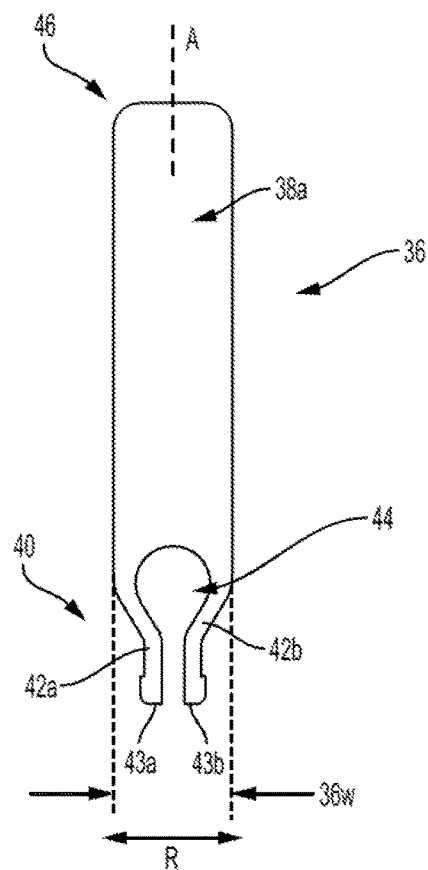
FIG. 3 is a top view of one embodiment of a retainer plate.
Figure 4:
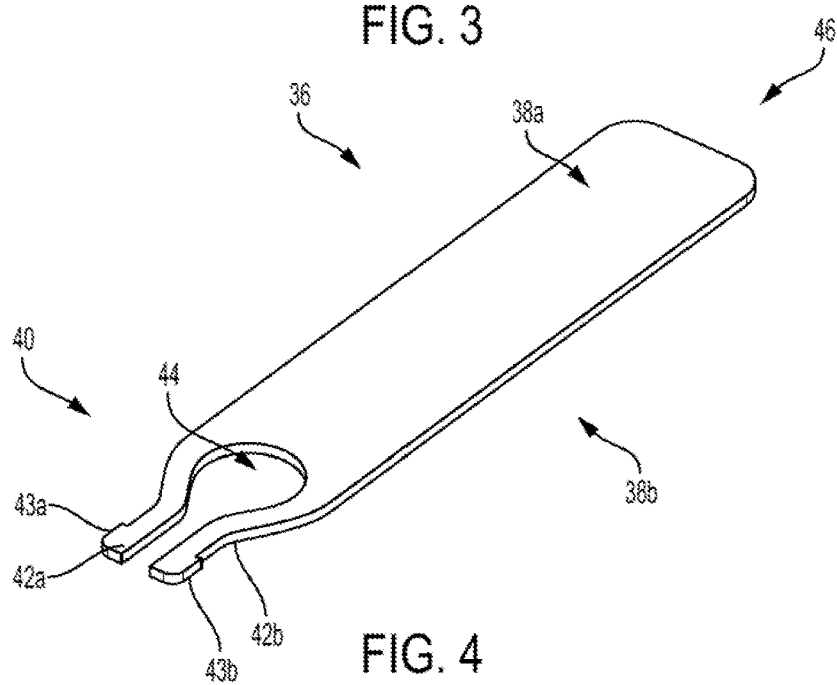
FIG. 4 is a perspective view of the plate of FIG. 3.

FIGS. 3 and 4 illustrate one embodiment of a retainer plate 36 configured to facilitate manipulation of a suture. As discussed herein, the plate 36 can be configured to be removably and replaceably seated in a surgical instrument (e.g., in an upper jaw of an end effector of the instrument). The plate 36 can have a variety of sizes, shapes, and configurations.

The plate 36 can be formed from a variety of materials. The material(s) forming the plate 36 can be selected to allow the plate 36 to deform without breaking, e.g., to bend or flex without breaking. In an exemplary embodiment, the material(s) can be biocompatible. In an exemplary embodiment, the plate 36 can be metallic, e.g., formed from one or more metals. The plate 36 being metallic may provide structural stability to the plate 36 while allowing the plate 36 to deform without breaking.

The plate 36 can be disposable. In other words, after the plate 36 is removed from a surgical instrument in which the plate 36 is seated, the plate 36 can be disposed of according to applicable standards of discarding used medical devices or elements thereof. The plate 36 being disposable may help prevent the adverse effects of metal fatigue that can arise from reuse of a metallic plate. In an exemplary embodiment, the plate 36 can be disposed of after a single use, which may prevent any deformation of the plate 36 that occurs during use from adversely affecting subsequent use of the plate 36 and/or may prevent the adverse effects of metal fatigue that can arise from reuse of a metallic plate since such adverse effects typically do not arise during a single use.

As shown, the plate 36 can be a planar member having substantially flat top and bottom surfaces 38a, 38b. A person skilled in the art will appreciate that a surface may not be precisely flat but nevertheless be considered to be substantially flat due to, e.g., manufacturing tolerances, a texture thereon, and/or tolerances in measurement devices. The plate 36 being planar may facilitate loading of the plate 36 into a surgical instrument, which is described further below.

The plate 36 can include a pair of arms 42a, 42b at a proximal end 40 of the plate 36. The arms 42a, 42b can extend longitudinally, as shown. The arms 42a, 42b can taper inwardly, e.g., toward a longitudinal axis A of the plate 36, so as to be located within a maximum width 36w defined by the plate 36. The arms 42a, 42b can define an opening 44 therebetween. The arms 42a, 42b can be configured to be laterally movable, as shown by arrow R in FIG. 3. The opening 44 between the arms 42a, 42b provides room for the arms 42a, 42b to laterally move. The arms 42a, 42b being laterally movable may facilitate the loading of the plate 36 into a surgical instrument, as discussed further below. In general, the arms 42a, 42b can be configured to lock the plate 36 in position relative to the surgical instrument.

The arms 42a, 42b can have a normal or default position, which is shown in FIGS. 3 and 4. The arms 42a, 42b can each be configured to move laterally from the default position and dynamically return to the default position, similar to a spring, absent an external force applied thereto holding one or both of the arms 42a, 42b in a position other than the default position.

The arms 42a, 42b at their respective proximal ends can each have a protrusion 43a, 43b extending radially outward therefrom. The protrusions 43a, 43b can be configured to facilitate seating of the plate 36 in an end effector of a surgical instrument, as discussed further below.

As shown, a distal-most surface 46 of the plate 36 can be linear, e.g., straight. In other embodiments, a retainer plate's distal-most surface can be non-linear. In general, the non-linear distal-most surface can be configured as a suture retention feature. The plate's distal-most surface being non-linear may help the plate grip a suture being captured by the surgical instrument in which the plate is loaded, as discussed further below, and thereby help retain the suture.

The plate 36 can have a variety of shapes. As shown, the plate 36 can have a substantially rectangular distal portion from which the arms 42a, 42b extend in a proximal direction.

Figure 5:
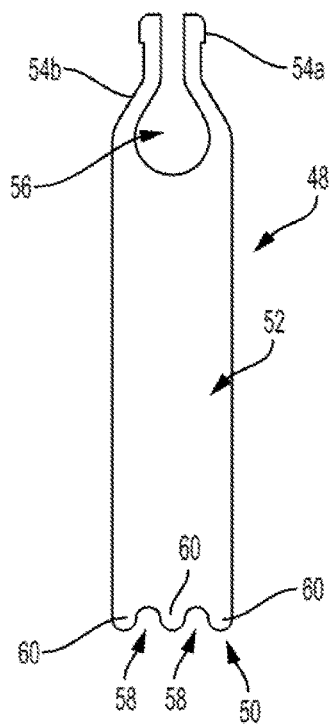
FIG. 5 is a top view of another embodiment of a retainer plate.

FIG. 5 illustrates one embodiment of a retainer plate 48 having a non-linear distal-most surface 50. The plate 48 can otherwise be configured and used similar to the plate 36, e.g., can have a substantially flat top surface 52 and a substantially flat bottom surfaces (obscured in FIG. 5), can be metallic, can include a pair arms 54a, 54b defining an opening 56 therebetween, etc. The distal-most surface 50 in this illustrated embodiment is a wavy surface defining a plurality of suture-seating grooves 58 therein and a plurality of teeth 60. The grooves 58 can each be configured to seat a suture therein, e.g., a suture being captured by the instrument in which the plate 48 is seated, and/or to "bite" into the suture. The wavy surface defines curved shapes of the grooves 58 and the teeth 60. The curved shape of the grooves 58 and the teeth 60 may help prevent a suture from snagging, tearing, or otherwise becoming damaged by the plate's distal-most surface 50. Sutures typically have circular cross-sections, so the curved shape of each of the grooves 58 may match the shape of a suture, which may help urge the suture into the grooves 58.

Figure 6:
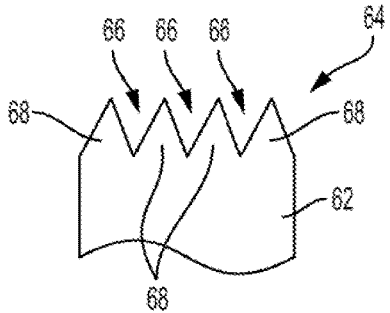
FIG. 6 is a top view of a distal portion of another embodiment of a retainer plate.
Figure 6A:
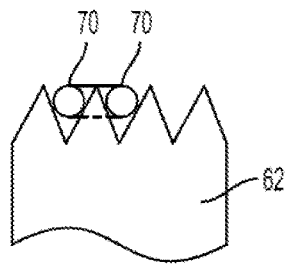
FIG. 6A is a top view of the distal portion of the plate of FIG. 6 having a suture coupled thereto.

FIG. 6 illustrates another embodiment of a retainer plate 62 having a non-linear distal-most surface 64. The plate 62 can otherwise be configured and used similar to the plate 36. In this illustrated embodiment, the distal-most surface 64 has a triangular wave shape defining a plurality of triangular grooves 66 and a plurality of triangular teeth 68. The triangular shape of the grooves 66 may help crimp a suture therein, since sutures typically have a circular cross-sectional shape. FIG. 6A shows one embodiment of a suture 70 seated in two of the grooves 66 and straddling one of the teeth 68. In other words, the suture 70 is looped over one of the teeth 68. Such seating of the suture 70 can be how the suture 70 is positioned relative to the plate 62 when the suture 70 is captured by an instrument in which the plate 62 is seated. Alternatively, one or more of the teeth 68 can "bite" into the suture 70 to help retain the suture.

Figure 7:
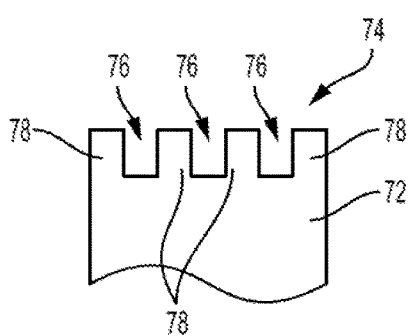
FIG. 7 is a top view of a distal portion of yet another embodiment of a retainer plate.

FIG. 7 illustrates another embodiment of a retainer plate 72 having a non-linear distal-most surface 74. The plate 72 can otherwise be configured and used similar to the plate 36. In this illustrated embodiment, the distal-most surface 74 has a square wave shape defining a plurality of square grooves 76 and a plurality of square teeth 78. The square shape of the grooves 76 may help grasp a suture similar to the triangular teeth 68.

In addition to or in alternative to a retainer plate having a non-linear distal-most surface configured as a suture retention feature, the plate can include one or more other types of suture retention features. Examples of other suture retention features include a textured surface, a surface finish, and a checkered surface.

Figure 8:
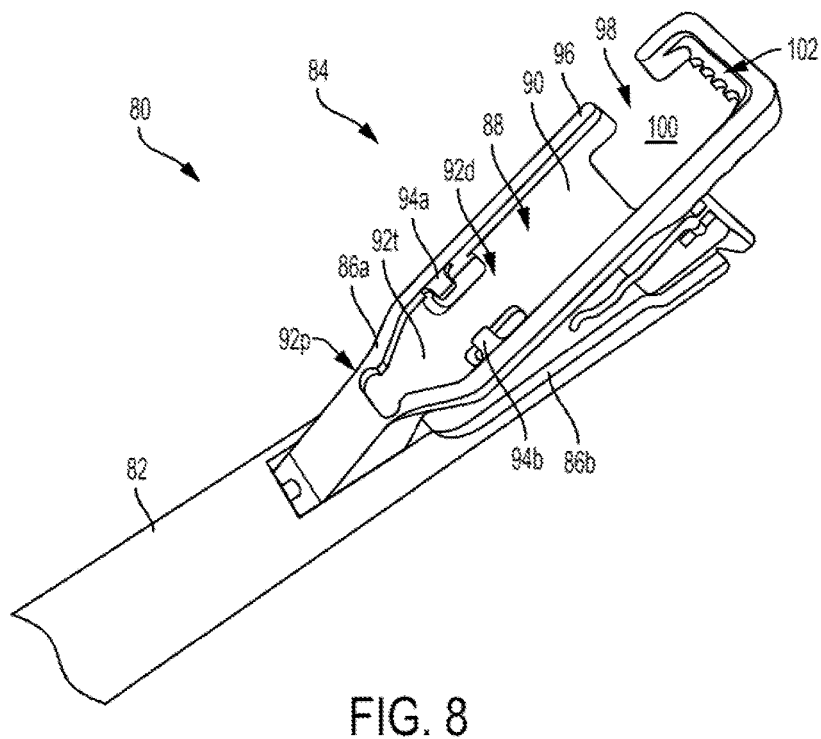
FIG. 8 is a perspective view of a distal portion of another embodiment of a surgical instrument configured to pass a suture through tissue.
Figure 9:
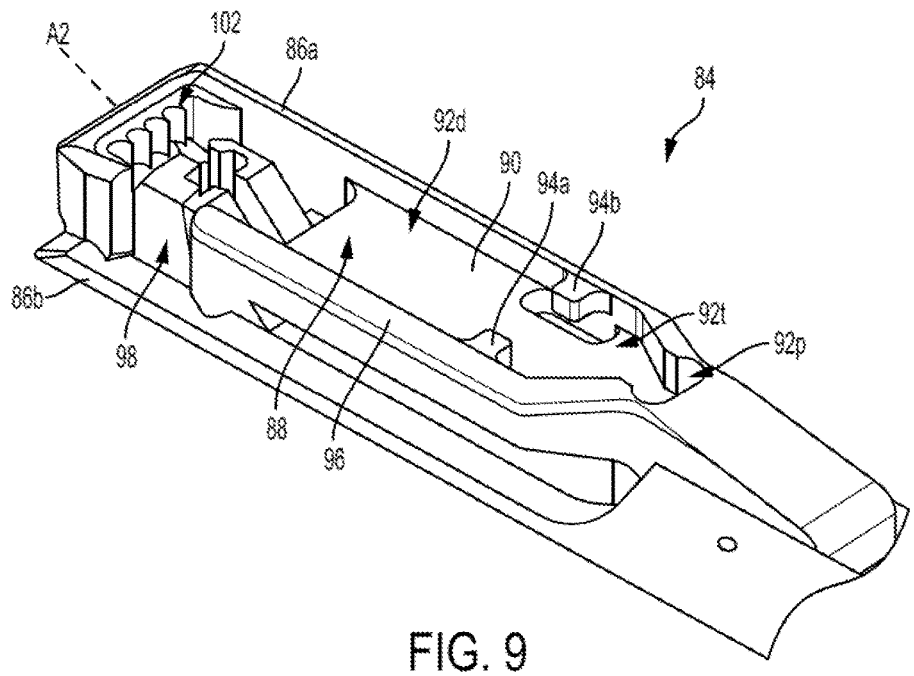
FIG. 9 is a perspective view of part of the distal portion of the surgical instrument of FIG. 8.

FIGS. 8 and 9 illustrate a distal portion of one embodiment of a surgical instrument 80 configured to facilitate passage of a suture through tissue and including an end effector 84 configured to seat a retainer plate (not shown) therein. The instrument 80 can generally be configured and used similar to the instrument 10 of FIG. 1 and other surgical instruments described herein, e.g., include a handle portion (not shown), include an elongate shaft 82 having the end effector 84 at a distal end thereof, be configured to removably and replaceably seat a needle (not shown), etc. In this illustrated embodiment, the end effector 84 includes upper and lower jaws 86a, 86b, with the upper jaw 86a being configured to move relative to the lower jaw 86b and the elongate shaft 82. FIG. 8 shows the jaws 86a, 86b in an open position, and FIG. 9 shows the jaws 86a, 86b in a closed position.

Figure 10:
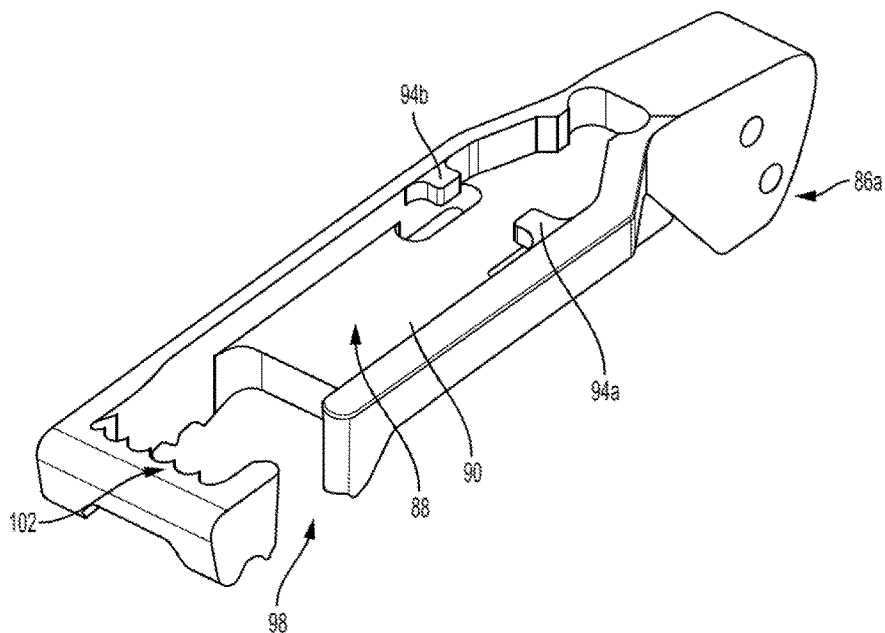
FIG. 10 is a perspective view of an upper jaw of the surgical instrument of FIG. 8.

The upper jaw 86a, which is shown as a standalone element in FIG. 10, can be configured to removably and replaceably seat the retainer plate therein. An outer or upper side of the upper jaw 86a can be configured to seat the plate in a cavity 88 formed in the upper side. The upper side of the upper jaw 86a being configured to seat the plate may facilitate visualization of the plate within the upper jaw 86a, which may help a user visually confirm proper loading of the plate into the end effector 84 since the plate may be visible in the end effector 84 regardless of whether the jaws are open or closed and regardless of whether any material (e.g., tissue, etc.) is positioned between the jaws. The cavity 88 can define a recessed portion of the upper jaw 86a configured to seat the plate therein. The cavity 88 can extend longitudinally along the upper jaw 86a and hence longitudinally along the end effector 84, with reference to a longitudinal axis A2 of the end effector 84. The upper jaw 86a can thus be disposed between the plate and the lower jaw 86b when the plate is seated in the upper jaw 86a. The cavity 88 can include a bottom surface 90 configured to seat the plate thereon. The bottom surface 90 can be substantially flat and therefore correspond in shape to a substantially flat surface of the plate. The substantially flat surface of the plate, e.g., one of substantially flat top and bottom surfaces of the plate, can thus be configured to rest on the substantially flat bottom surface 90.

The cavity 88 can have a shape corresponding to a shape of a retainer plate configured to be seated in the upper jaw 86a. As shown, the cavity 88 has a shape corresponding to shapes of the plate 36 of FIG. 3 and the plate 48 of FIG. 5. Namely, the cavity 88 has a substantially rectangular shape in a distal portion 92d thereof and has a tapered proximal portion 92t that tapers proximally to a smaller width. The distal portion 92d of the cavity 88 can be configured to seat a substantially rectangular portion of the plate, and the tapered proximal portion 92t of the cavity 88 can be configured to seat the plate's tapering arms therein. A proximal-most portion 92p of the cavity 88 proximal to the tapered proximal portion 92t can expand from a minimum width of the cavity 88 define by the tapered proximal portion 92t. The proximal-most portion 92p of the cavity 88 can be configured to seat the proximal-most ends of the plate's arms therein. The proximal-most portion 92p of the cavity 88 can thus be configured to seat protrusions at proximal ends of the plate's arms therein. The cavity 88 having a greater width in its proximal-most portion 92p than at least at the proximal end of the tapered proximal portion 92t of the cavity 88 can facilitate locking of the plate therein. The protrusions of the plate's arms can be configured to be seated in the proximal-most portion 92p of the cavity 88, which may help hold the plate within the cavity 88 at a fixed longitudinal position. In other words, the arms' protrusions and the upper jaw 86a can cooperate to hold the plate within the upper jaw 86a at a fixed axial position. The plate's arms can be configured to be compressed radially inward from the arms' normal or default position within the cavity 88 such that the arms are dynamically urged radially outward within the cavity 88. This radially outward directed force may help hold the plate within the cavity 88, and hence within the upper jaw 86a and the end effector 84, and help prevent the plate from moving laterally within the cavity 88 once seated therein.

The upper jaw 86a can include a plate-retaining feature configured to help retain the plate within the upper jaw 86a, e.g., within the upper jaw's cavity 88. As shown, the plate-retaining feature can include retention tabs 94a, 94b. The illustrated upper jaw 86a includes two retention tabs 94a, 94b, but an upper jaw can include another number of plate-retaining features (e.g., one, three, four, etc.). The retention tabs 94a, 94b can extend radially inward, e.g., toward the end effector's longitudinal axis A2, from a top surface of the upper jaw 86a, e.g., from an upper rim or perimeter 96 thereof, so as to be positioned above the cavity 88. Thus, the plate seated within the cavity 88 will be below the retention tabs 94a, 94b. The retention tabs 94a, 94b can thus be configured to help retain the plate within the cavity 88 by preventing upward movement of the plate within the cavity 88 at least at a location of the tabs 94a, 94b along the longitudinal axis A2. The retention tabs 94a, 94b can be located adjacent the tapered proximal portion 92t of the cavity 88, e.g., within the tapered proximal portion 92t, at a junction between the tapered proximal portion 92t and the distal portion 92d, or within the distal portion 92d in a proximal region thereof. The plate seated in the upper jaw 86a may thus deform without being limited by the retention tabs 94a, 94b, as discussed further below.

The upper rim 96 of the upper jaw 86a can be non-continuous so as to not fully extend around the upper jaw 86a. In other words, the upper jaw 86a can have a gap 98 (also referred to herein as a "window") formed therein. The gap 98 may facilitate visualization of a plate within the upper jaw 86a, which may help a user visually confirm proper loading of the plate into the end effector 84 since the plate may be visible in the end effector 84 regardless of whether the jaws are open or closed and regardless of whether any material (e.g., tissue, etc.) is positioned between the jaws. The gap 98 can be in communication with the cavity 88 such that material such as a suture can pass through the gap 98 and into the cavity 88 and/or from the cavity 88 and out of the gap 98. This passage may facilitate grasping of a suture by the end effector 84, as discussed further below. The bottom surface 90 of the cavity 88 can exist only in a proximal portion of the upper jaw 86a, as shown, such that an area 100 distal to the bottom surface 90 is open adjacent to the gap 98. The open area 100 may also facilitate grasping of a suture by the end effector 84. The gap 98 can be formed in a side of the upper jaw 86a between its proximal and distal ends, as shown, to facilitate side-removal of a suture from the upper jaw 86a, e.g., removal of the suture transversely (e.g., perpendicular or at another non-right or non-zero angle) to the end effector's longitudinal axis A2. A person skilled in the art will appreciate that the direction may not be precisely perpendicular but nevertheless be considered to be substantially perpendicular due to, e.g., manufacturing tolerances, a texture thereon, and/or tolerances in measurement devices.

The upper jaw 86a can include a suture-retaining feature configured to facilitate retention of a suture by the end effector 84. As shown, the suture-retaining feature can include a non-linear interior surface 102, e.g., an interior-facing surface, at a distal end of the upper jaw 86a. The non-linear interior surface 102 can generally be configured similar to a non-linear distal-most surface of a plate, such as the non-linear distal-most surfaces 50, 64, 74 discussed above, and can include a plurality of grooves and a plurality of teeth. The upper jaw's non-linear interior surface 102 has a wavy shape similar to the wavy shape of the non-linear distal-most surface 50 of FIG. 5 discussed above. The non-linear interior surface 102 can be recessed within the upper jaw 86a, as shown. This recessing can allow the non-linear interior surface 102 to be aligned with a distal-most surface of the plate seated in the cavity 88. The plate's non-linear distal-most surface and the upper jaw's non-linear interior surface 102 can thus be configured to grip a suture therebetween to help the end effector 84 securely hold the suture. In other words, the upper jaw's suture-retaining feature 102 can be configured to cooperate with a distal-most surface of the plate seated in the cavity 88 to facilitate the surgical instrument's grasping of a suture.

Figure 11:
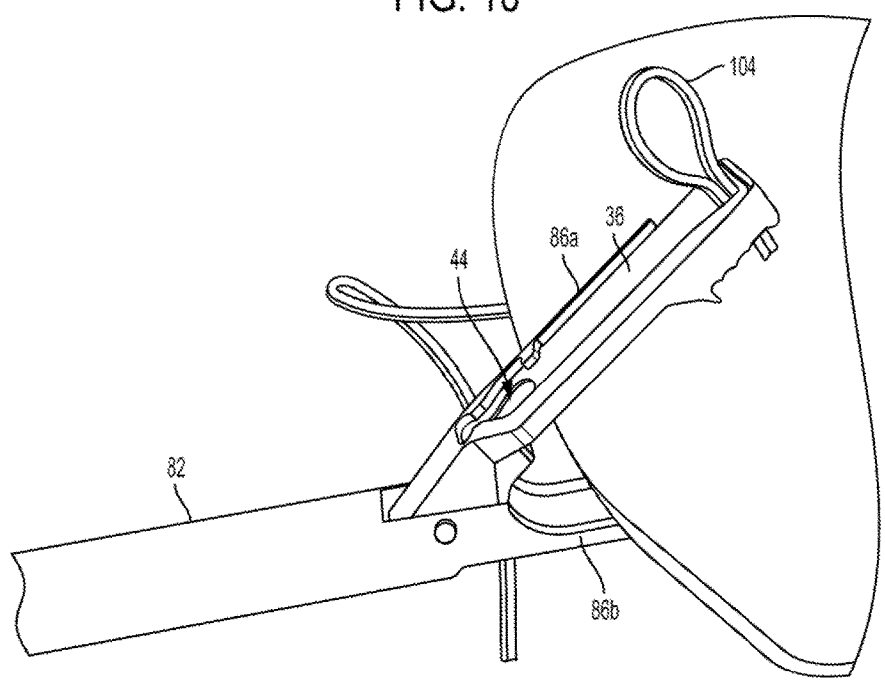
FIG. 11 is a perspective view of the surgical instrument of FIG. 8 having the plate of FIG. 3 loaded therein, engaging a suture, and engaging a material representative of tissue.
Figure 12:
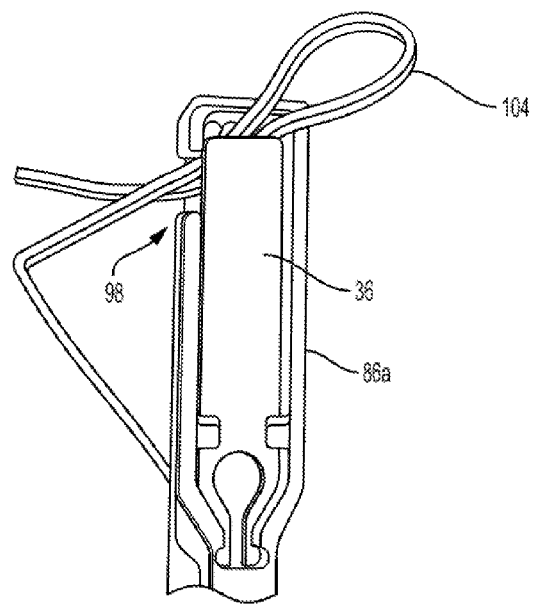
FIG. 12 is a top view of the surgical instrument of FIG. 11 having the plate loaded therein and having the suture being removed from the surgical instrument.
Figure 13:
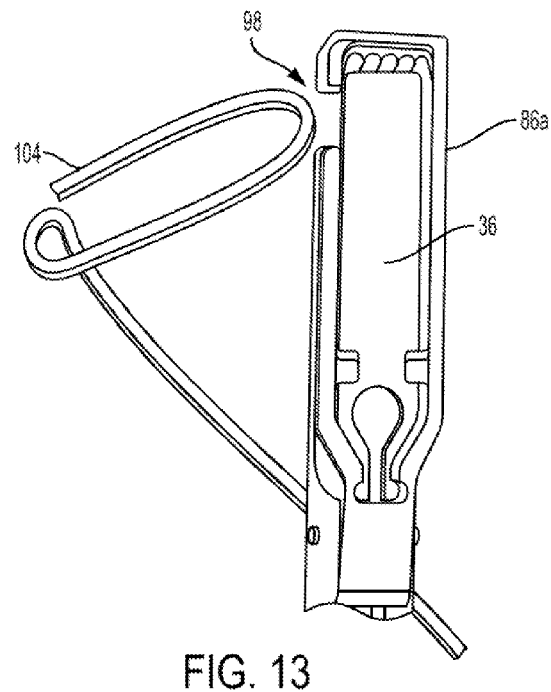
FIG. 13 is a top view of the surgical instrument of FIG. 12 having the plate loaded therein and having the suture removed from the surgical instrument.

By way of example, FIG. 11 shows the plate 36 of FIG. 3 seated in the cavity 88 of the upper jaw 86a of FIG. 8 with the end effector 84 in an open position and grasping a suture 104 passed through material 106 representative of tissue. The end effector 84 can, however, seat other types of plates, e.g., a plate similar to the plate 36 but formed from a different material, the plate 48 of FIG. 5, etc. The suture 104 is extending through the opening 100 and is gripped between the plate's distal-most surface 46 and the upper jaw's non-linear interior surface 102. As discussed further below, the suture 104 grasped by the end effector 84 can be pulled by the instrument away from the material 106, e.g., away from tissue, through which the suture 104 extends. The suture 104 can then be moved through the gap 98, as shown in FIG. 12, to be removed from the end effector 84, as shown in FIG. 13.

Figure 14:
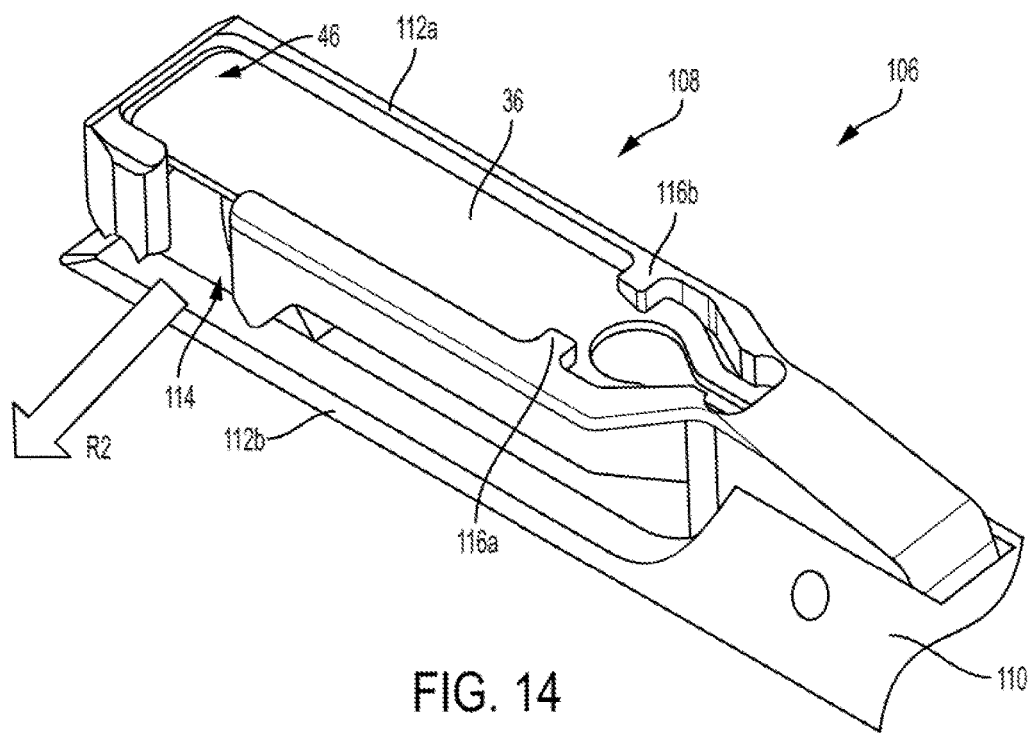
FIG. 14 is a perspective view of a distal portion of yet another embodiment of a surgical instrument configured to pass a suture through tissue, the surgical instrument having the plate of FIG. 3 loaded therein.

FIG. 14 illustrates a distal portion of another embodiment of a surgical instrument 106 configured to facilitate passage of a suture through tissue and including an end effector 108 configured to seat a retainer plate therein. The plate 36 of FIG. 3 is shown seated in the end effector 108 that includes upper and lower jaws 112a, 112b, but other types of plates can be seated therein, e.g., a plate similar to the plate 36 but formed from a different material, the plate 48 of FIG. 5, etc. The instrument 106 can generally be configured and used similar to the instrument 10 of FIG. 1 and other surgical instruments described herein, e.g., include a handle portion (not shown), include an elongate shaft 110 having the end effector 108 at a distal end thereof, be configured to removably and replaceably seat a needle (not shown), etc. The upper jaw 112a can generally be configured and used similar to the upper jaw 86a of FIG. 8 and other upper jaws described herein. In this illustrated embodiment, the upper jaw 112a is configured to move relative to the lower jaw 112b and the elongate shaft 110. FIG. 14 shows the jaws 112a, 112b in a closed position. An arrow R2 in FIG. 14 indicates a direction in which a suture (not shown) grasped by the end effector 108 may be moved through a gap 114 formed in a side of the upper jaw 112a.

A size of a cavity (obscured in FIG. 14) formed in the upper jaw 112a and a size of plate to be seated in the upper jaw 112a can be chosen so that no clearance space exists between the upper's jaw's suture-retaining feature, e.g., a linear or non-linear interior-facing surface at a distal end the upper jaw 112a. The interior-facing surface at the distal end the upper jaw 112a is obscured in FIG. 14 because no clearance space exists between this surface and the plate's distal-most surface 46. In other words, the plate 36 overlaps the suture-retaining feature, e.g., the interior-facing surface at the distal end the upper jaw 112a. The lack of clearance space between the upper jaw's interior-facing surface and the plate's distal-most surface 46 may facilitate grasping of a suture therebetween. As mentioned above, the plate 36 can be configured to deform. This deformation can be in an upward direction, with retention tabs 116a, 116b of the upper jaw 112a helping to keep the plate 36 retained in the upper jaw 112a, as discussed above. A suture captured by the instrument 106 can be "trapped" between the deformed plate's distal-most surface 46 and the upper jaw's interior-facing surface, thereby facilitating the instrument's grasp of the suture. Additionally, the plate's lack of distal-most surface 46 being linear, as opposed to be non-linear, may not affect the grasp of the suture due to the lack of clearance space. If clearance space does exist between the upper jaw's interior-facing surface and a distal-most surface of a plate seated in the upper jaw 112a, the plate's distal-most surface being non-linear can be configured to facilitate suture grasping, as discussed above, such that the lack of clearance space may not affect the grasp of the suture.

Figure 15:
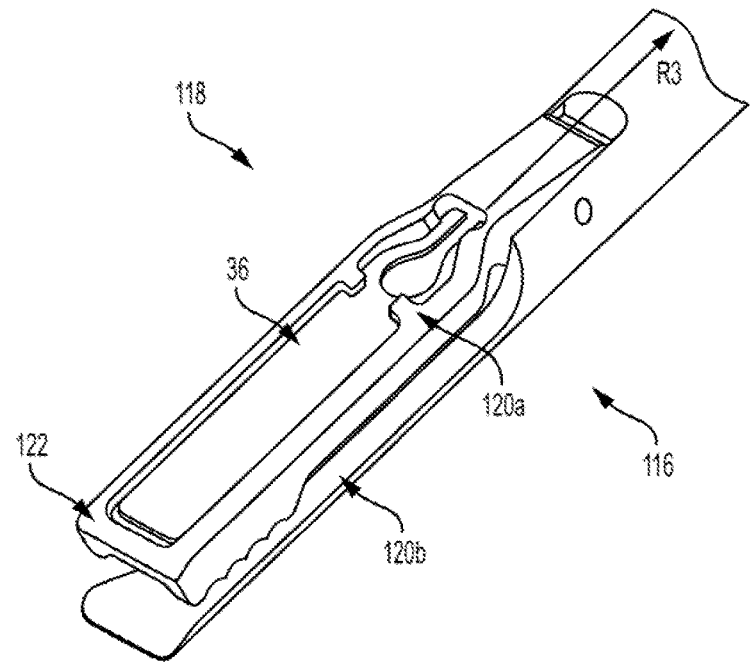
FIG. 15 is a perspective view of a distal portion of still another embodiment of a surgical instrument configured to pass a suture through tissue, the surgical instrument having the plate of FIG. 3 loaded therein.

FIG. 15 illustrates a distal portion of another embodiment of a surgical instrument 117 configured to facilitate passage of a suture through tissue and including an end effector 118 configured to seat a retainer plate therein. The plate 36 of FIG. 3 is shown seated in the end effector 118 that includes upper and lower jaws 120a, 120b, but other types of plates can be seated therein, e.g., a plate similar to the plate 36 but formed from a different material, the plate 48 of FIG. 5, etc. The instrument 117 is like the instrument 106 of FIG. 14 except that the instrument 117 does not include a sidewall gap like the gap 114. Instead, an upper rim 122 of the upper jaw 120 is continuous so as to extending fully around the upper jaw 120a.

FIG. 15 also illustrates an arrow R3 pointing proximally and indicating a direction of loading of the plate 36 into the end effector 118, e.g., into the upper jaw 120a. Such loading can be accomplished using a loading element, as discussed further below.

Figure 16:
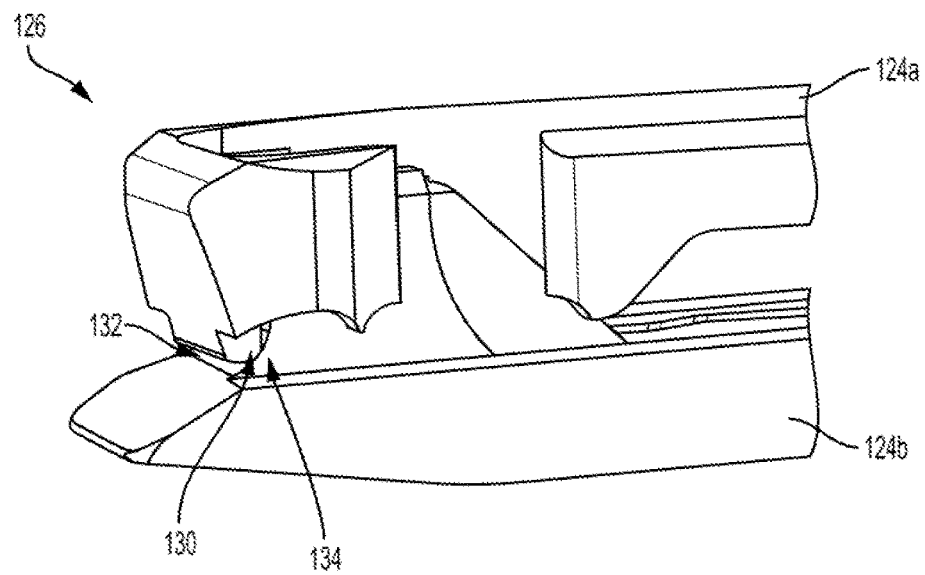
FIG. 16 is a perspective cross-sectional view of a distal portion of one embodiment of an end effector of a surgical instrument configured to pass a suture through tissue.
Figure 17:
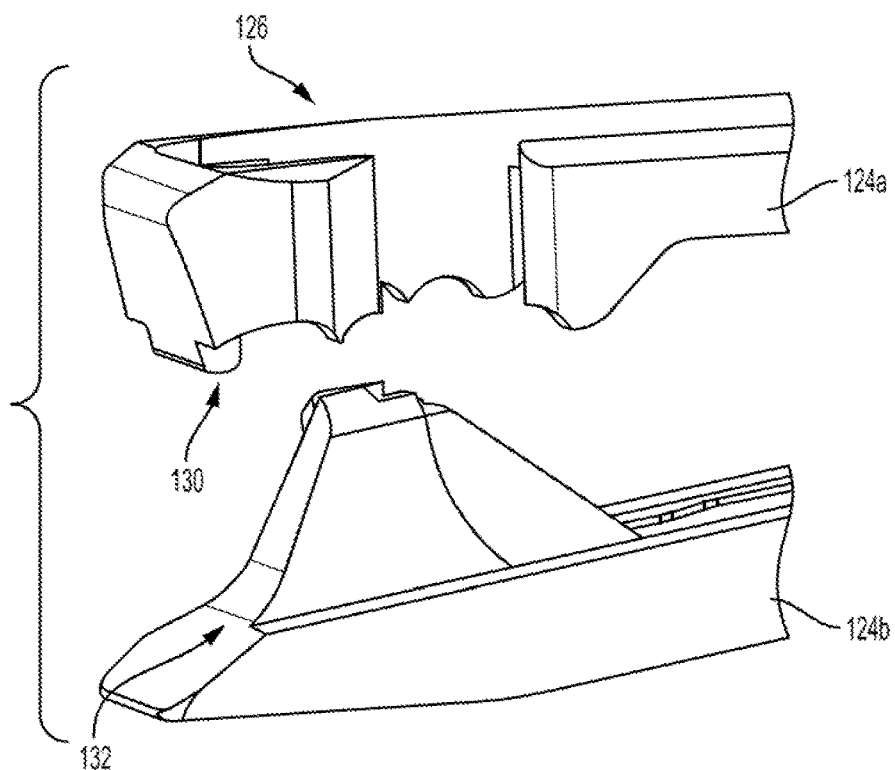
FIG. 17 is a another perspective cross-sectional view of the distal portion of the end effector of FIG. 16.
Figure 18:
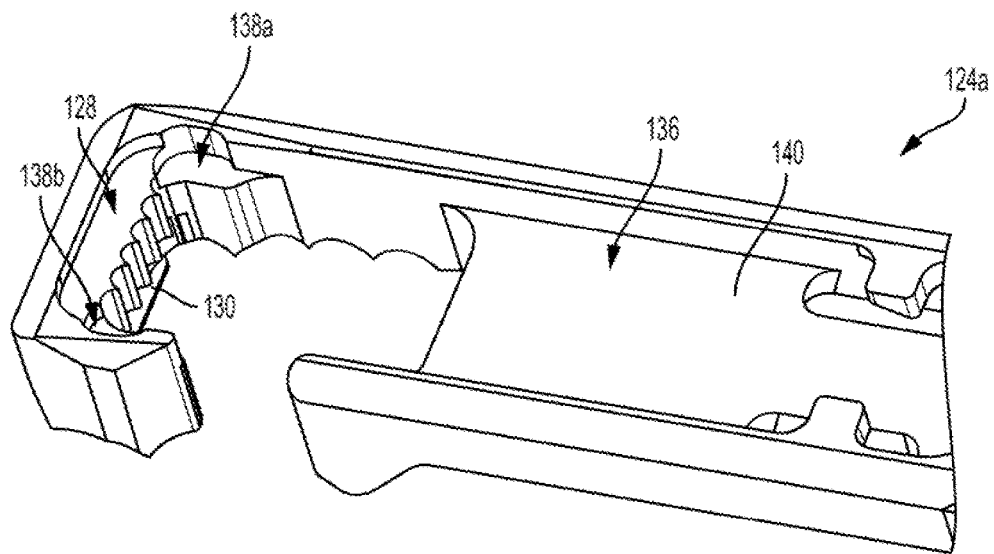
FIG. 18 is a perspective view of a distal portion of a top jaw of the end effector of FIG. 16.
Figure 19:
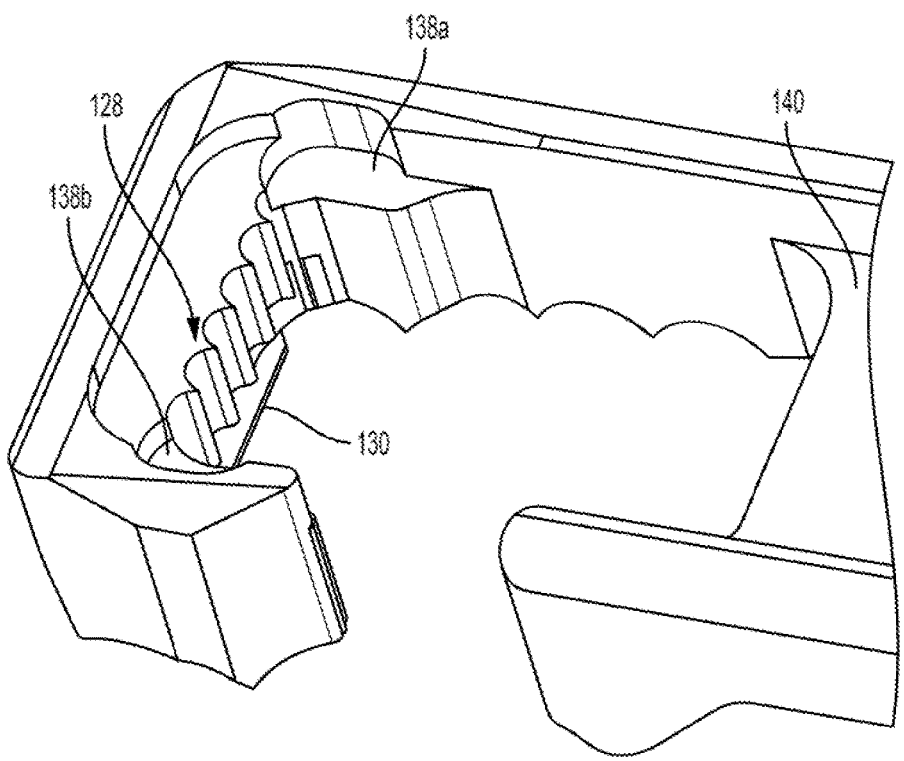
FIG. 19 is an enlarged view of part of the distal portion of the top jaw of FIG. 16.

FIGS. 16-19 illustrate another embodiment of an upper jaw 124a configured to seat a retainer plate (not shown) therein. FIGS. 16 and 17 also illustrate a bottom jaw 124b of an end effector 126 that also includes the upper jaw 124a. The end effector 126 can generally be configured and used similar to the end effector 16 of FIG. 1 and other end effectors described herein. The end effector 126 can thus be part of an instrument that can be configured and used similar to the instrument 10 of FIG. 1 and other surgical instruments described herein, e.g., include a handle portion (not shown), include an elongate shaft (not shown) having the end effector 126 at a distal end thereof, be configured to removably and replaceably seat a needle (not shown), etc. The end effector 126 is shown in a closed position in FIG. 16 and in an open position in FIG. 17. For clarity of illustration, only distal portions of the end effector 126 are shown in FIGS. 16 and 17, and only distal portions of the upper jaw 124a are shown in FIGS. 18 and 19.

The upper jaw 124a can generally be configured and used similar to the upper jaw 86a of FIG. 8 and other upper jaws described herein. However, in this illustrated embodiment, the upper jaw 124a includes a secondary suture-retaining feature in addition to the suture-retaining feature of a non-linear interior surface 128 at a distal end of the upper jaw 124a. In general, the secondary suture-retaining feature can be configured to facilitate retention of a suture by the end effector 126. The secondary suture-retaining feature in this illustrated embodiment includes a bucktooth 130. As shown in FIGS. 16 and 17, the bucktooth 130 can extend downwardly toward the bottom jaw 124b and can be located at a distal-most end of the upper jaw 124a. The bucktooth 130 can thus define a downwardly protruding portion of the upper jaw 124a at the distal-most end thereof. The bottom jaw 124b can include a suture-engaging surface 132 facing the bucktooth 130, e.g., an upwardly facing surface that faces the downwardly-extending bucktooth 130. An area 134 between the suture-engaging surface 132 and the bucktooth 130 can be an area in which a suture grasped by the end effector 126 is clamped or pinched between the suture-engaging surface 132 and the bucktooth 130 so as to provide an increased retention force to the suture over the retention force provided by the non-linear interior surface 128 and the retention plate (not shown) seated in the upper jaw 124a. This clamping or pinching may help the end effector 126, and hence the surgical instrument of which it is part, securely hold onto the suture, such as during pull-out of the suture from a patient's body. The upper jaw 124a includes a single bucktooth 130, which may help ensure that the suture grasped by the end effector 126 is clamped or pinched between the bucktooth 130 and the suture-engaging surface 132, as opposed to being more loosely disposed between different buckteeth.

Also unlike the upper jaw 86a of FIG. 8, in this illustrated embodiment, the upper jaw 124a includes a stepped area configured to prevent downward deformation of a retention plate seated in the upper jaw 124a, e.g., within a cavity 136 formed in an upper side of the upper jaw 124a. The stepped area in this illustrated embodiment includes two stepped areas 138a, 138b on opposed left and right sides of the upper jaw 124a, but an upper jaw can include another number of stepped areas (e.g., one, three, four, etc.). The stepped area 138a, 138b can be stepped downwardly from the upper jaw's non-linear interior surface 128, as shown. The stepped area 138a, 138b can thus be configured as a stop surface that prevents the plate seated in the upper jaw 124a from deforming downwardly beyond a certain point defined by the stepped area 138a, 138b. The stepped area 138a, 138b may thus help maintain relatively close vertical distance between the plate's distal-most surface and the upper jaw's non-linear interior surface 128, which as discussed herein can cooperate together to grasp a suture therebetween. The stepped area 138a, 138b can be located in a distal portion of the upper jaw 124a and thereby be configured to seat a distal portion of the plate. The stepped area 138a, 138b can thus be configured to prevent downward deformation of a distal portion of the plate seated in the upper jaw 124a. A bottom surface 140 of the cavity 136 on which the plate is seated can be similarly configured to prevent downward deformation of a proximal portion the plate seated in the upper jaw 124a.

In at least some embodiments, a retention plate can be pre-loaded into an end effector of a surgical instrument, e.g., loaded therein during manufacturing, such that a user receives the instrument with the plate loaded therein. The plate may thus be properly loaded into the instrument since it is loaded therein according to manufacturing specifications and/or the plate may be less likely to be dropped or lost when removing the plate from its packaging. The plate can be removably and replaceably pre-loaded into the end effector such that the plate can be removed from the end effector by a user (e.g., a surgeon, a surgical assistant, a medical technician, etc.) and replaced therein with a second plate. The second plate can then be removed from the end effector by the user or another user and replaced therein with a third plate, and so on. However, as discussed above, it may be difficult to load the second plate and any subsequent plates into the instrument, e.g., into the instrument's end effector, for one or more reasons. Similarly, in embodiments in which an end effector of a surgical instrument does not have a retention plate pre-loaded therein such that a first plate loaded into the end effector is manually loaded therein by a user, it may be difficult to load the first plate and any subsequently loaded plates into the instrument, e.g., into the instrument's end effector, for one or more reasons.

Figure 20:
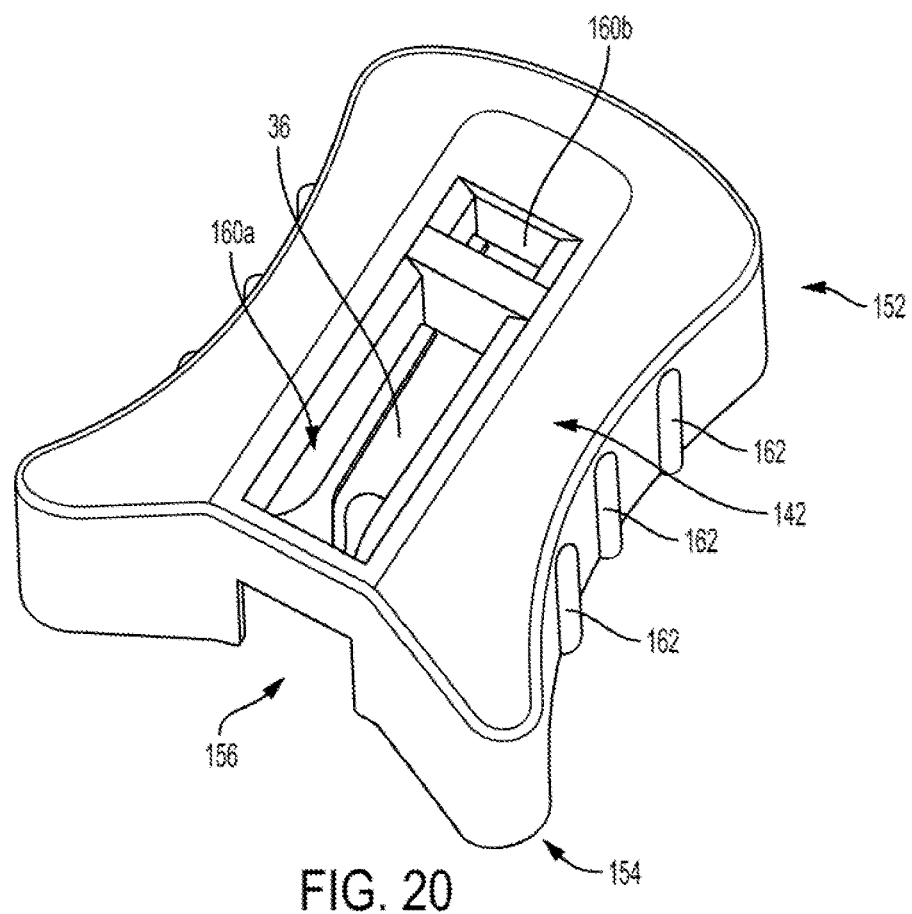
FIG. 20 is a perspective view of one embodiment of a loading element, the loading element having the plate of FIG. 3 seated therein.
Figure 21:
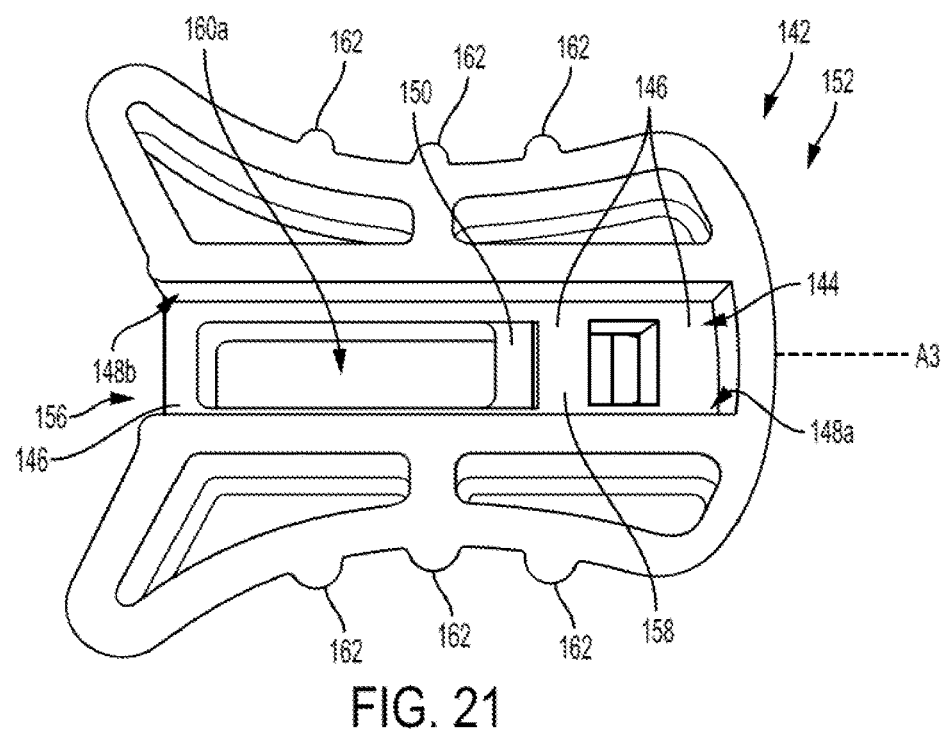
FIG. 21 is a bottom view of the loading element of FIG. 20 without the plate seated therein.

As mentioned above, a loading element can be configured to facilitate the loading of a retention plate into a surgical instrument. FIGS. 20 and 21 illustrate one embodiment of a loading element 142 configured to facilitate loading of a plate into a surgical instrument (not shown) configured to pass a suture through tissue. The loader 142 is shown in FIG. 20 with the plate 36 of FIG. 3 and is discussed below relative thereto, but the loader 142 can be used with this plate 36 and/or other plates, e.g., a plate similar to the plate 36 but formed from a different material, the plate 48 of FIG. 5, the plate 72 of FIG. 7, etc. The loader 142 can be configured to have the plate 36 loaded therein for delivery of the plate 36 to a surgical instrument. The plate 36 can be pre-loaded therein, e.g., during manufacturing. The plate 36 may thus be properly loaded into the loader 142 since it is loaded therein according to manufacturing specifications. Alternatively, the loader 142 may not have the plate 36 pre-loaded therein, and the plate 36 can be manually loaded into the loader 142 by a user. The user may thus select by preference a particular plate.

The loader 142 can be disposable. In other words, after the loader 142 is used to load the plate 36 into a surgical instrument, the loader 142 can be disposed of according to applicable standards of discarding used medical devices or elements thereof. The loader 142 being disposable may limit improper loading of a retention plate therein, and hence improper delivery of the plate to a surgical instrument, since the loader 142 can be pre-loaded with a plate and disposed after the one loading of the one plate into a surgical instrument.

The loader 142 can include a cavity 144 formed in a bottom side thereof, as shown in FIG. 21. The cavity 144 can be configured to seat the plate 36 therein and to receive at least a portion of an end effector therein simultaneously with the plate 36 being seated therein. The portion of the end effector receivable in the cavity 144 can include at least a portion of the end effector, e.g., an upper jaw thereof, configured to seat the plate 36 therein. As discussed in further detail below, movement of the loader 142 relative to the end effector at least partially seated therein (or movement of the end effector relative to the loader 142 having the end effector at least partially seated therein) can cause the plate 36 seated in the loader 142 to move from being seated in the loader 142 to being seated in the end effector. The plate 36 may thus be easily loaded into the end effector using the loader 142. No loading accessories other than the single loader 142 may be needed to accomplish the loading of the plate 36 into the end effector, thereby reducing equipment costs and/or resulting in a simple plate-loading procedure.

A proximal end 154 of the loader 142 can have an opening 156 formed therethrough that is in communication with the cavity 144. The opening 156 can be configured to have a portion of a surgical instrument extending therethrough when at least a portion of the surgical instrument is seated within the cavity 144, e.g., when at least a portion of the instrument's upper jaw is seated within the cavity 144 to receive the plate 36 therein.

The cavity 144 can have a lower surface 146 and opposed side surfaces 148a, 148b. A distance between the opposed side surfaces 148a, 148b can be configured to allow a clearance fir between the loader 142 and the portion of the end effector (e.g., upper jaw) to be positioned within the cavity 144 to have the plate 36 loaded therein. A distance between the opposed side surfaces 148a, 148b can thus be slightly larger than a width of an upper jaw of an end effector. The lower surface 146 of the cavity 144 can be configured to seat thereon an upper surface of an end effector's upper jaw having at least a portion thereof positioned within the cavity 144. The upper surface of the upper jaw and the lower surface 146 of the cavity 144 can be slidably engaged. Depending on a longitudinal length of the end effector's upper jaw, the upper jaw may not be seated on an entirety of the lower surface 146.

Figure 22:
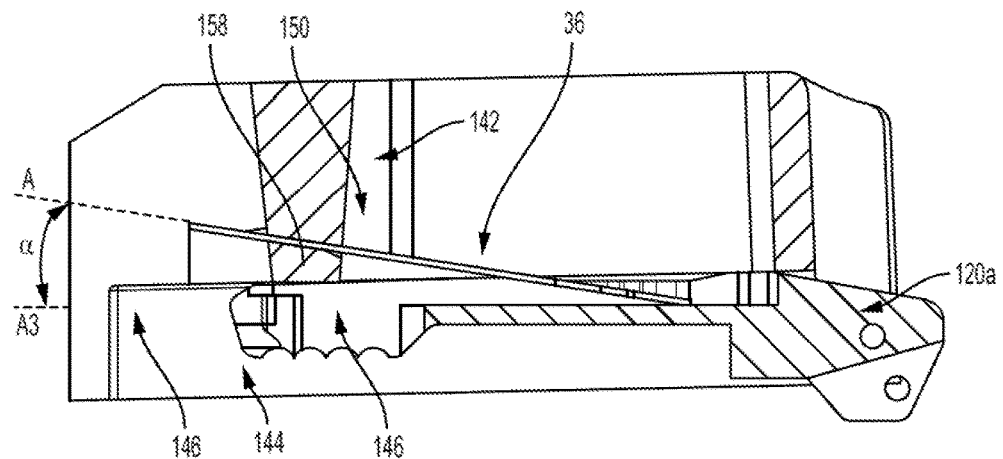
FIG. 22 is a side cross-sectional schematic view of the loading element and the plate of FIG. 20, the loading element having a distal portion of an upper jaw of an end effector seated therein.

Below the cavity's lower surface 146, the loader 142 can include a plate-seating surface 150 configured to seat the plate 36 thereon. The plate-seating surface 150 can be angled in a distal direction toward a distal end 152 of the loader 142. The plate 36, when seated on the plate-seating surface 150, can thus be positioned within the cavity 144 at an angle, as shown in FIG. 22. A longitudinal axis A3 of the loader 142 and the longitudinal axis A of the plate 36 can thus be at an angle α. The angle α can have any of a variety of non-zero values greater than 0° and less than 90°. The plate-seating surface 150 can thus also have any of a variety of non-zero values greater than 0° and less than 90°, since the angle of the plate-seating surface 150 defines the angle α. The plate 36 being angled in the loader 142 prior to the plate's loading into an end effector using the loader 142 may help the plate 36 be positioned within an upper jaw of an end effector under retention tabs thereof, instead of above the retention tabs, such that the retention tabs can be effective to retain the plate 36 within the upper jaw.

The loader 142 can include a crossbar 158 that is distal to the plate-seating surface 150. A portion of the lower surface 146 of the cavity 144 can define a portion of the crossbar 158, as shown in FIGS. 21 and 22. The crossbar 158 can extend substantially perpendicular to the longitudinal axis A3 of the loader 142, and hence to the longitudinal axis A of the plate 36 when the plate 36 is seated in the cavity 144 of the loader 142. A person skilled in the art will appreciate that the extension may not be precisely perpendicular but nevertheless be considered to be substantially perpendicular due to, e.g., manufacturing tolerances and/or tolerances in measurement devices. The crossbar 158 can be configured as a support to help hold the plate 36 in the loader 142 prior to the plate's loading into an end effector.

The loader 142 can include a window 160a, 160b formed in a top side thereof. The window 160a, 160b in this illustrated embodiment includes two windows. The window 160a, 160b can be in communication with the cavity 144, thereby allowing visualization of the cavity 144 through the window 160a, 160b. If matter is positioned within the cavity 144, such as the plate 36 and/or a portion of an end effector, the matter can be visualized through the window 160a, 160b. The window 160a, 160b may thus facilitate proper loading of the plate 36 into an end effector since the plate 36 and/or the end effector can be visually inspected when located within the loader 142.

The loader 142 can include a grip mechanism 162 configured to facilitate manual handling of the loader 142 by improving grip of the loader 142. The grip mechanism 162 in this illustrated embodiment includes raised external surface features on opposed sides of the loader 142. Other examples of grip mechanisms include a textured surface and finger depressions. The loader 142 can include any number of grip mechanisms. Curved sides of the loader 142 between the loader's proximal and distal ends 154, 152, as shown, may facilitate the loader 142 being held by fingers at the curved sides.

FIG. 22 also shows the upper jaw 120a of the end effector 118 of FIG. 15 positioned within the cavity 144 prior to the plate 36 having moved to be seated in the upper jaw 120a. The loader 142 may be used with this end effector 118 and/or other end effectors, e.g., the end effector 84 of FIG. 8, the end effector 126 of FIG. 16, etc.

Figure 23:
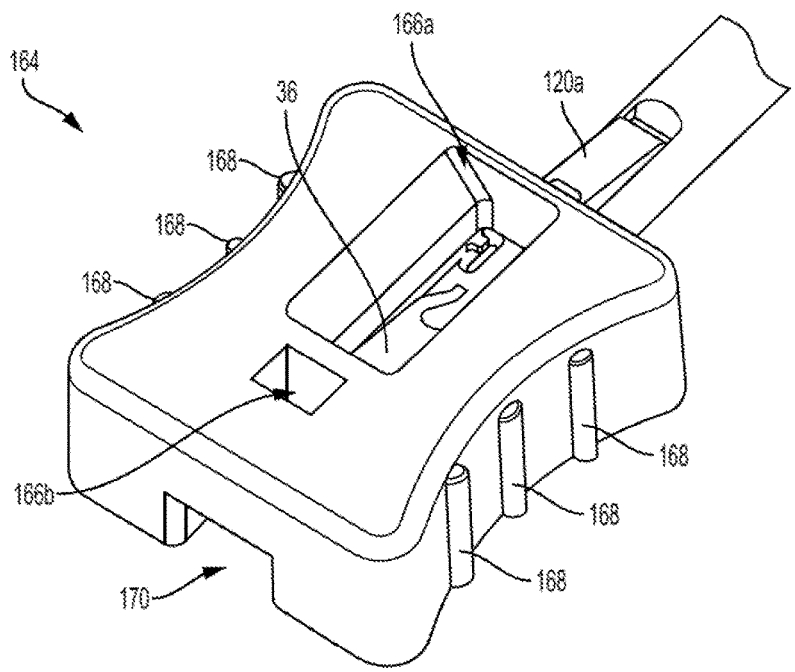
FIG. 23 is a perspective view of another embodiment of a loading element, the loading element having the plate of FIG. 3 seated therein and having a distal portion of the surgical instrument of FIG. 15 seated therein.

FIG. 23 illustrates another embodiment of a loading element 164 configured to facilitate loading of a plate 36 into a surgical instrument 117 configured to pass a suture through tissue. The loader 164 is shown with the plate 36 of FIG. 3 and the instrument 117 of FIG. 15 and is discussed below relative thereto, but the loader 164 may be used with this plate 36 and/or other plates, e.g., a plate similar to the plate 36 but formed from a different material, the plate 48 of FIG. 5, the plate 72 of FIG. 7, etc., and may be used with this instrument 117 and/or other instruments, e.g., the instrument 80 of FIG. 8, etc. The loader 164 can generally be configured and used similar to the loader 142 of FIG. 20, e.g., include a window 166*a*, 166*b*, include a grip mechanism 168, include a cavity 170 therein, include a crossbar (obscured in FIG. 23), etc. In this illustrated embodiment, the loader 164 has a different overall shape than the loader 142 of FIG. 20. Also in this illustrated embodiment, the cavity 170 has an open distal end 170*d*, whereas the cavity 144 of the loader 142 of FIG. 20 has a closed distal end. The open distal end 170*d* may facilitate visualization of the plate 36 and/or the end effector 118 within the cavity 170 and thereby help a user evaluate proper loading of the plate 36 into the end effector 118, e.g., into the upper jaw 120*a*.

FIGS. 24-28 illustrate a method of using the loader 142 to load the plate 36 into another embodiment of a surgical instrument 172 configured to pass a suture through tissue. The instrument 172 can generally be configured and used similar to the instrument 10 of FIG. 1 and other surgical instruments described herein, e.g., include a handle portion (not shown), include an elongate shaft 174 having an end effector 176 at a distal end thereof, be configured to removably and replaceably seat a needle (not shown), etc. In this illustrated embodiment, the end effector 176 includes upper and lower jaws 178*a*, 178*b*, with the upper jaw 178*a* being configured to move relative to the lower jaw 178*b* and the elongate shaft 174. As mentioned above, the loader 142 can be used to load other plates into this instrument 172 and/or into other surgical instruments. Also, the loader 164 of FIG. 23 and other similar embodiments of loaders described herein can be used in a similar method.

As shown in FIG. 24, the loader 142 having the plate 36 seated in the cavity 144 thereof (the plate 36 and the cavity 144 are obscured in FIG. 24) can be advanced in a first direction, indicated by arrow D1, relative to the end effector 176 at the distal end of the instrument 172. The advancement can be due to the loader 142 moving relative to the end effector 176 or the end effector 176 moving relative to the loader 142. The first direction D1 is substantially perpendicular to the loader's longitudinal axis A3 and is substantially perpendicular to a longitudinal axis A4 of the upper jaw 178*a*. The upper jaw's longitudinal axis A4 is substantially parallel to a longitudinal axis A5 of the shaft 174, as shown in FIG. 24, when the end effector 176 is in a closed position. In FIG. 24 the end effector 176 is in the closed position, e.g., the jaws 178*a*, 178*b* are closed. A person skilled in the art will appreciate that the first direction D1 may not be precisely perpendicular to the axis A4 but nevertheless be considered to be substantially perpendicular due to, e.g., tolerances in measurement devices.

The loader 142 can be advanced in the first direction D1 toward the end effector 176 such that a distal tip 180 of the upper jaw 178*a* is seated in the cavity 144, since the plate 36 will be seated in the upper jaw 178*a*. A distal tip 182 of the bottom jaw 178*b* can also be seated in the cavity 144 such that a distal tip of the end effector 176 is seated in the cavity 144. An amount of the upper jaw's distal tip 180 positioned in the cavity 144 (and an amount of the bottom jaw's distal tip 182 if also positioned in the cavity 144) can vary. In general, enough of the upper jaw's distal tip 180 can be positioned in the cavity 144 such that some of the upper jaw 178*a* is within the cavity 144 and some of the upper jaw 178*a* is outside the cavity 144 with a portion of the upper jaw 178*a* being within the opening 156. Enough of the bottom jaw's distal tip 182 can be similarly positioned.

Figure 25A:
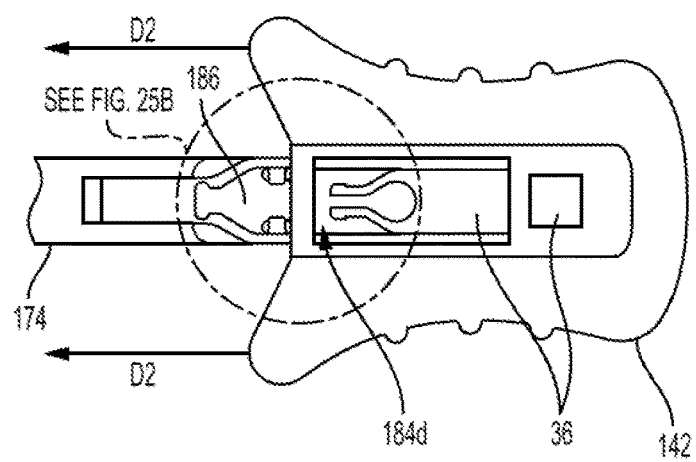
FIG. 25 is a top view of the loading element of FIG. 24 in a loading position on the surgical instrument of FIG. 24, including an enlarged inset.
Figure 25B:
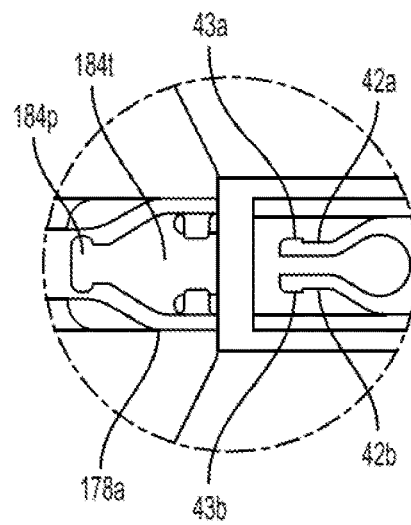

FIG. 25 shows the distal tips 180, 182 of the upper and lower jaws 178*a*, 178*b* seated in the cavity 144. As shown, the arms 42*a*, 42*b* of the plate 36 can be located within a distal portion 184*d* of a cavity 186 formed in an upper side of the upper jaw 178*a*. The arms 42*a*, 42*b* can thus be located distal to a tapered proximal portion 184*t* of the cavity 186 and to a proximal-most portion 184*p* of the cavity 186. The location of the plate 36, e.g., the arms 42*a*, 42*b* thereof, relative to the upper jaw 178*a* can be visually confirmed through the window 160*a* of the loader 142.

Figure 26:
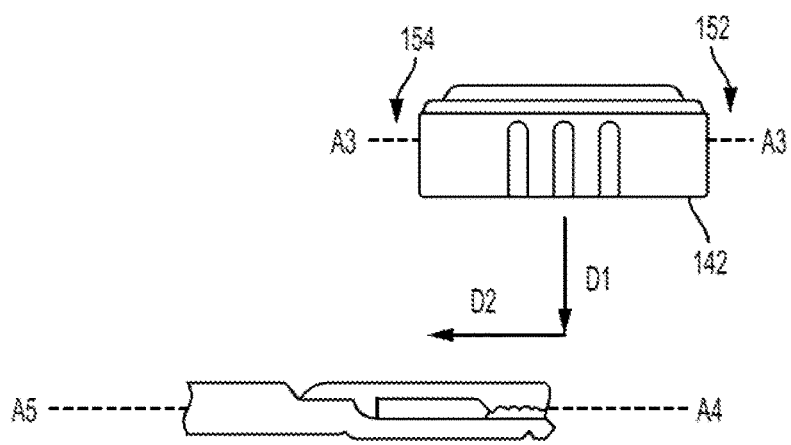
FIG. 26 is another side view of the loading element of FIG. 24 and of the distal portion of the surgical instrument of FIG. 24.

The loader 142 having been advanced in the first direction D1 toward the end effector 176 to seat the distal tip 180 of the upper jaw 178*a* (and also possibly the distal tip 182 of the bottom jaw 178*b*, as in this illustrated embodiment) in the cavity 144, the loader 142 can then be advanced in a second direction, indicated by arrows D2 in FIGS. 25 and 26, relative to the end effector 176. The advancement can be due to the loader 142 moving relative to the end effector 176 or the end effector 176 moving relative to the loader 142. The second direction D2 is substantially perpendicular to the first direction D1. The second direction D2 is thus substantially parallel to the loader's longitudinal axis A3 and substantially parallel to the longitudinal axis A4 of the upper jaw 178*a*. A person skilled in the art will appreciate that the first direction D1 may not be precisely perpendicular to the second direction D2 but nevertheless be considered to be substantially perpendicular due to, e.g., tolerances in measurement devices. Similarly, a person skilled in the art will appreciate that the second direction D2 may not be precisely parallel to the axis A4 but nevertheless be considered to be substantially parallel due to, e.g., tolerances in measurement devices.

Figure 27A:
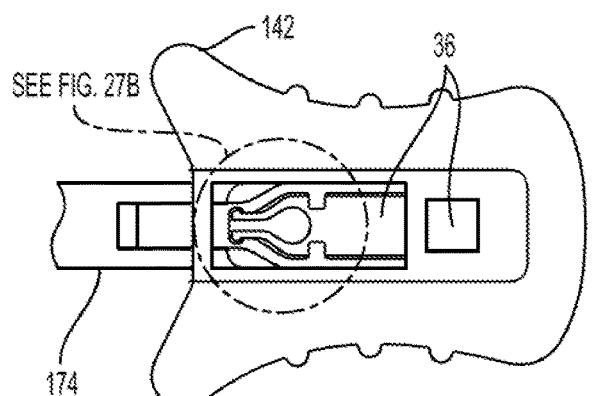
FIG. 27 is a top view of the loading element of FIG. 25 in a loaded position on the surgical instrument of FIG. 25, including an enlarged inset.
Figure 27B:
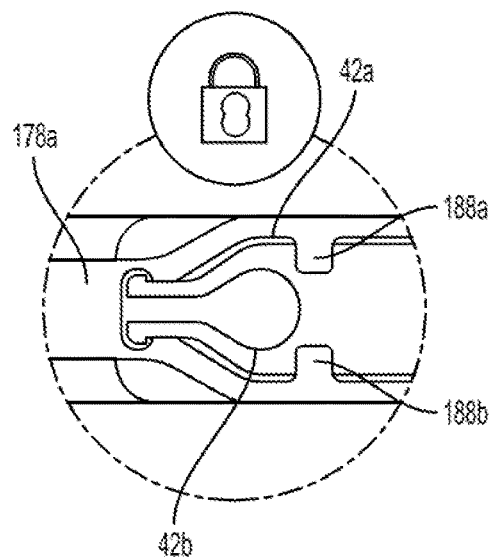

The advancement of the loader 142 in the second direction D2 can cause the arms 42*a*, 42*b* of the plate 36 to slide within the upper jaw's cavity 186 into and through the cavity's tapered proximal portion 184*t* and then into the cavity's proximal-most portion 184*p* within which the arms' protrusions 43*a*, 43*b* can be seated, as shown in FIG. 27. The protrusions 43*a*, 43*b* being seated in the cavity's proximal-most portion 184*p* can lock the plate 36 in the upper jaw 178*a*, as discussed above. The location of the plate 36, e.g., the arms 42*a*, 42*b* thereof, relative to the upper jaw 178*a* can be visually confirmed through the window 160*a* of the loader 142. The locking of the plate 36 within the upper jaw 178*a* can thus be visually confirmed. The angling of the plate 36 within the loader 142 prior to the plate 36 being seated in the end effector 176 can facilitate positioning of the plate 36 under the upper jaw's retention tabs 188*a*, 188*b* during the loader's advancement in the second direction D2.

Figure 28:
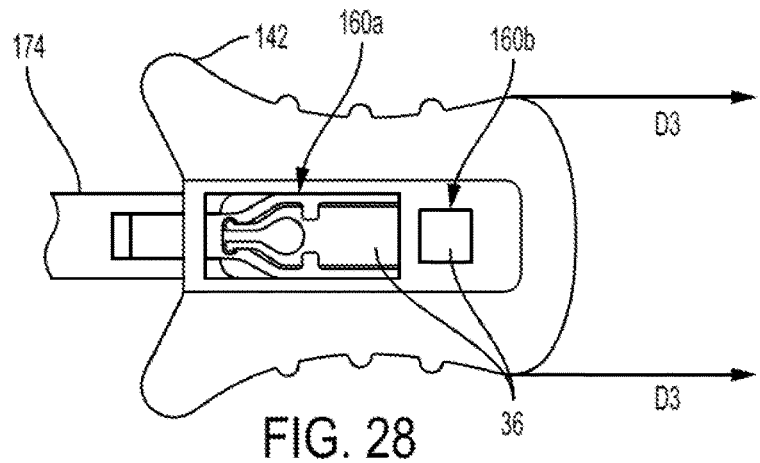
FIG. 28 is a top view of the loading element of FIG. 27 being removed from the surgical instrument of FIG. 27.

The plate 36 having been seated in the upper jaw 178*a*, e.g., locked therein, the loader 142 can be removed from the instrument 172. As shown in FIG. 28, the loader 142 can be removed from the instrument 172, with the plate 36 remaining in the upper jaw 178*a*, by the loader 142 being advanced in a third direction, indicated by arrows D3, relative to the end effector 176. The advancement can be due to the loader 142 moving relative to the end effector 176 or the end effector 176 moving relative to the loader 142. The third direction D3 is opposite to the second direction D2, e.g., the third direction D3 is a distal direction and the second direction D2 is proximal a direction. With the loader 142 removed from the instrument 172 and the plate 36 loaded into the end effector 176, the instrument 172 can be used in a surgical procedure to facilitate passage of suture through tissue, as discussed herein.

Figure 29:
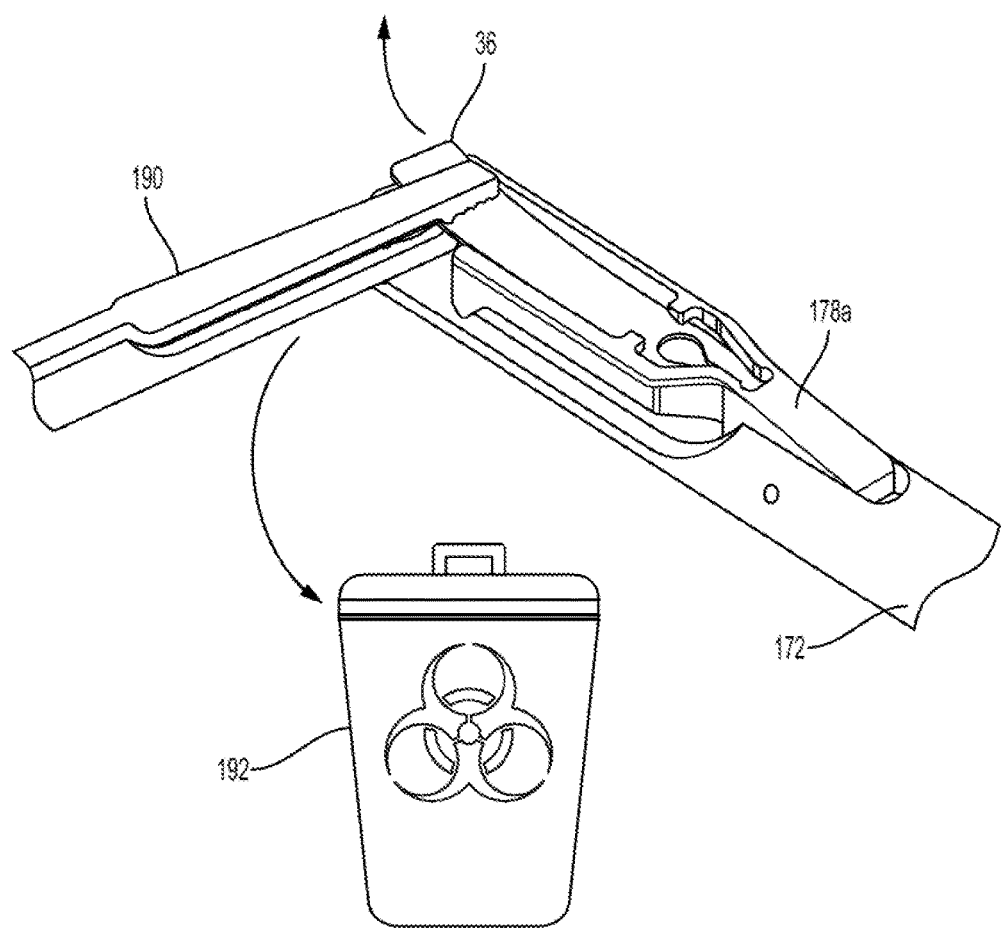
FIG. 29 is a perspective view of the plate of FIG. 28 being removed from the loading element of FIG. 28.
Figure 30:
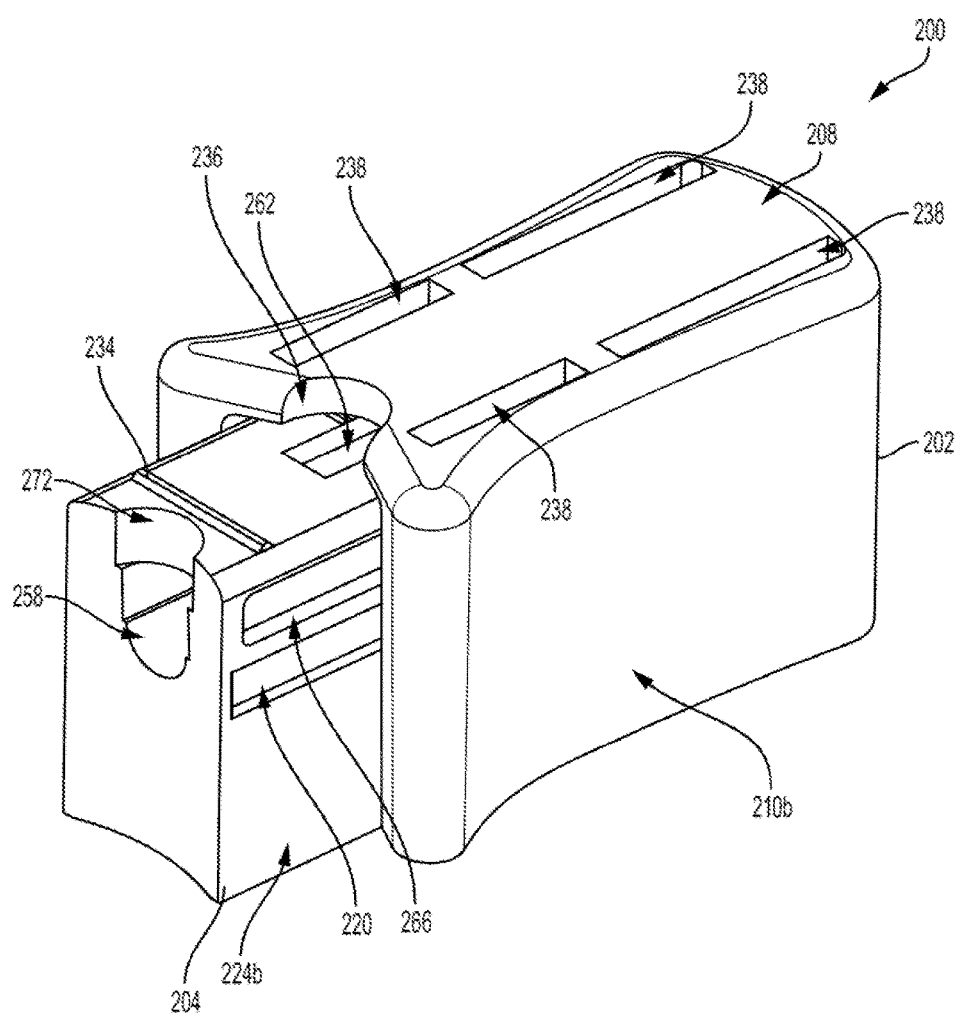
FIG. 30 is a perspective view of yet another embodiment of a loading element, the loading element including an inner member and an outer member.
Figure 31:
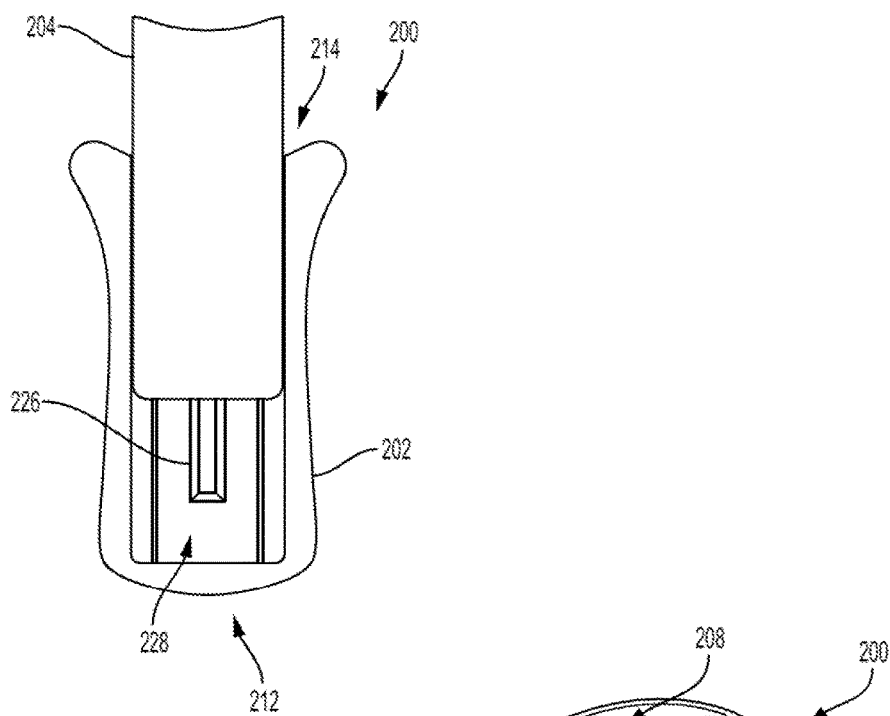
FIG. 31 is a bottom schematic view of the loading element of FIG. 30.
Figure 32:
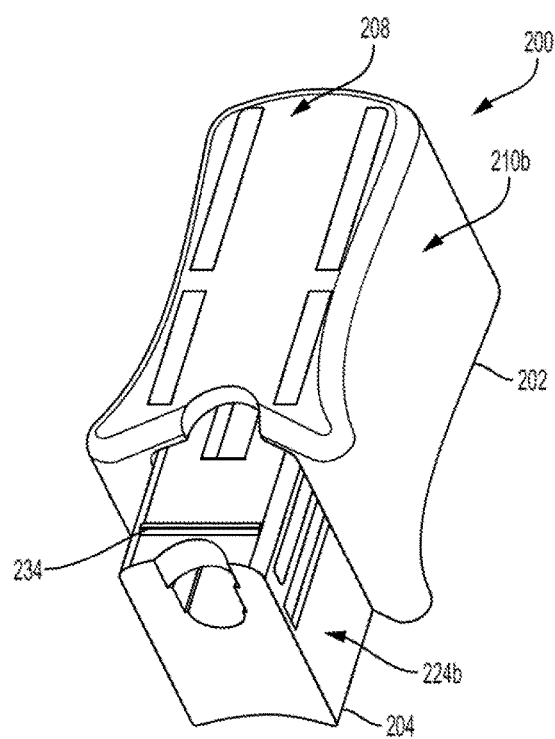
FIG. 32 is a perspective schematic view of the loading element of FIG. 30.

As mentioned above, the plate 36 can be removably and replaceably seated in the upper jaw 178a. The plate 36 can be removed from the upper jaw 178a in a variety of ways. FIG. 29 illustrates one embodiment of removing the plate 36 from the upper jaw 178a. As shown, a grasper 190 can grasp the plate 36 seated in the upper jaw 178a. Another tool (e.g., a hemostat, etc.) can be used instead of the grasper 190, or the plate 36 can be grasped by hand. The plate 36 can deform upward during use, as discussed herein, such that a distal portion of the plate 36 is bent upwards. This upwardly bent distal portion of the plate 36 may make the plate 36 easier to grasp for removal from the instrument 172. The grasper tool 190 (or other tool or hand), grasping the plate 36, can pull the plate 36 out of the upper jaw 178a. The removed plate 36 can then be disposed of in a medical waste bin 192 or otherwise per the appropriate medical waste disposal protocol.

The loaders 142, 164 of FIGS. 20 and 23 are each one-piece loading elements. A person skilled in the art will appreciate that a one-piece loader may include multiple pieces for assembly purposes, with the assemblage thereof resulting in the one-piece loader. In other embodiments, a loader can be a two-piece loading element that includes two independent one-piece loading members configured to cooperate with one another to load a retention plate into a surgical instrument. A person skilled in the art will appreciate that each of the loading members may include multiple pieces for assembly purposes, with the assemblage thereof resulting in the loading member. In general, the two-piece loader can be configured to receive a distal portion of a surgical instrument therein, and movement of one of the loading members relative to the other of the loading members can cause a plate seated in the loader to move from being seated in the loader to being seated in the distal portion of the surgical instrument received by the loader. The surgical instrument may then be removed from the loader with the plate remaining seated in the surgical instrument.

Figure 35:
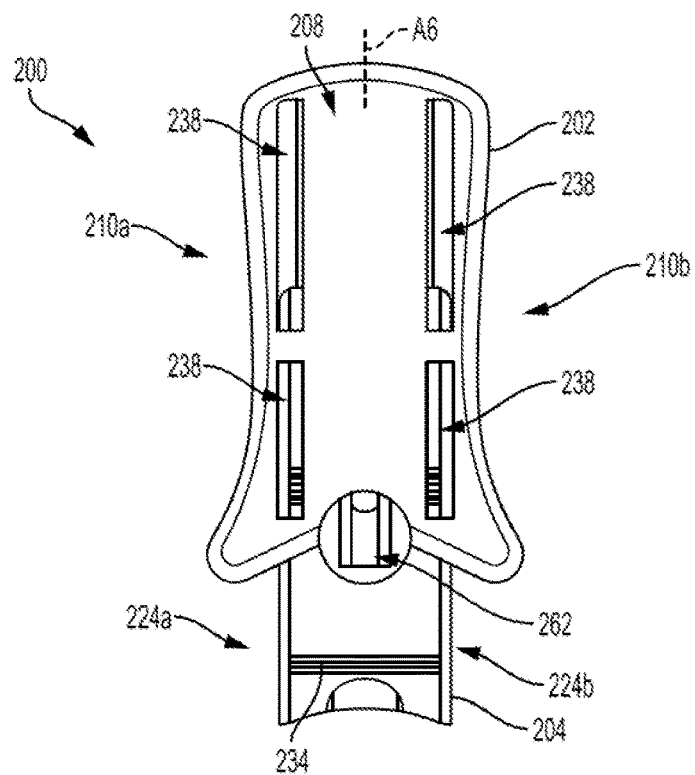
FIG. 35 is a top view of the loading element of FIG. 30.
Figure 36:
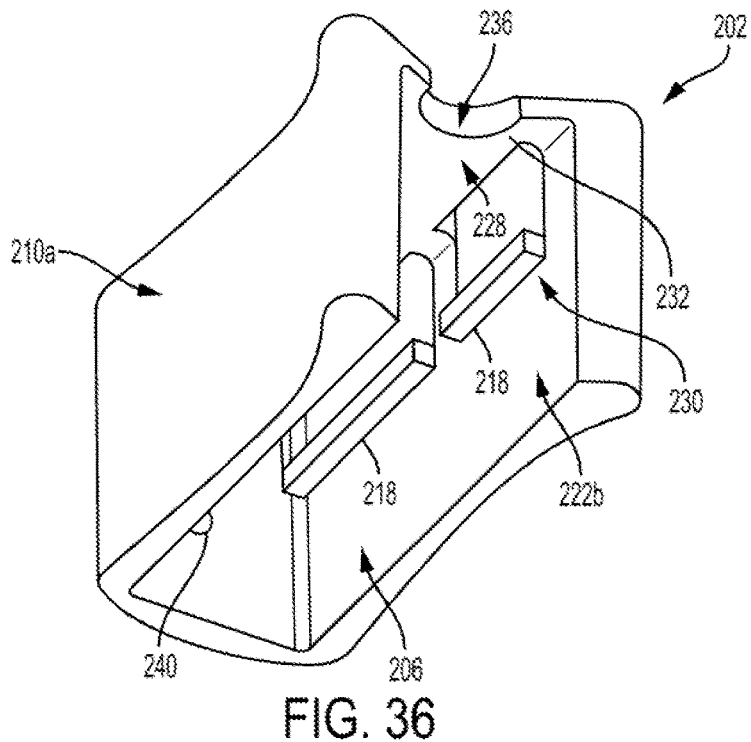
FIG. 36 is a perspective schematic view of the outer member of FIG. 30.
Figure 37:
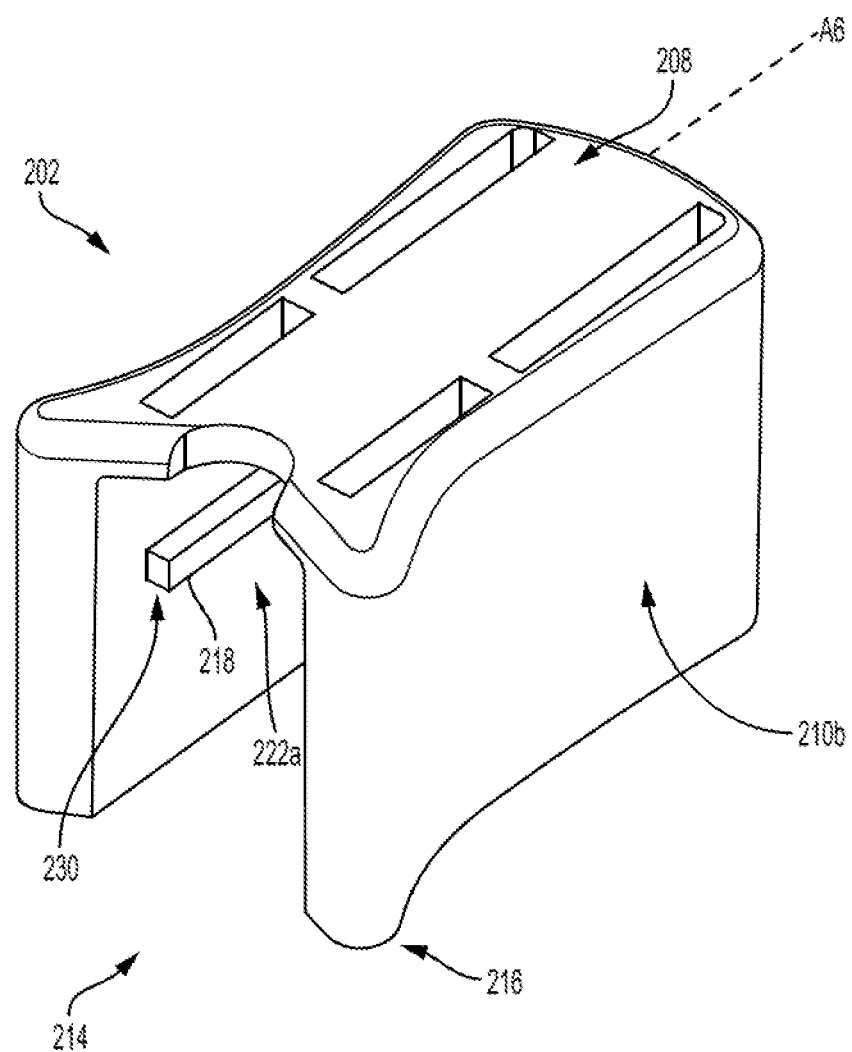
FIG. 37 is another perspective schematic view of the outer member of FIG. 36.
Figure 38:
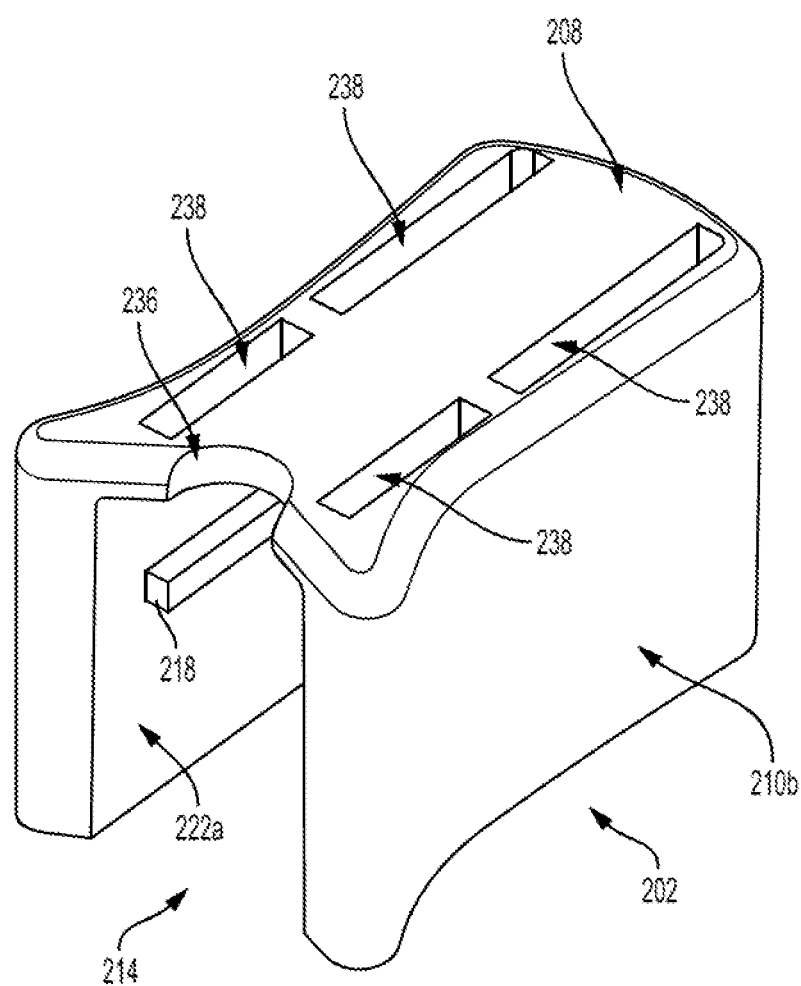
FIG. 38 is a perspective view of the outer member of FIG. 36.
Figure 39:
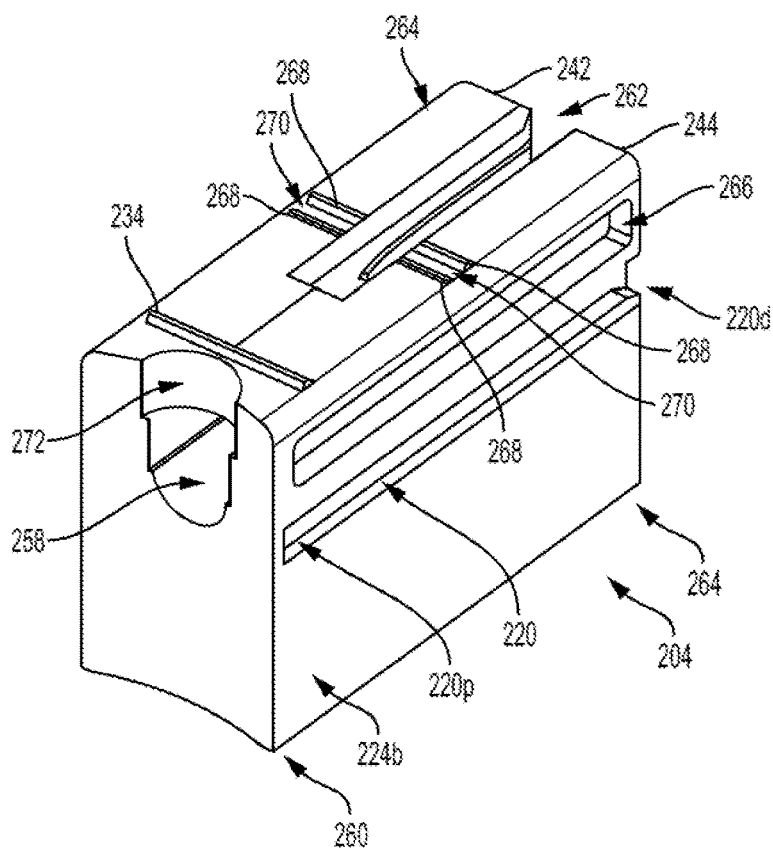
FIG. 39 is a perspective view of the inner member of FIG. 30.
Figure 40:
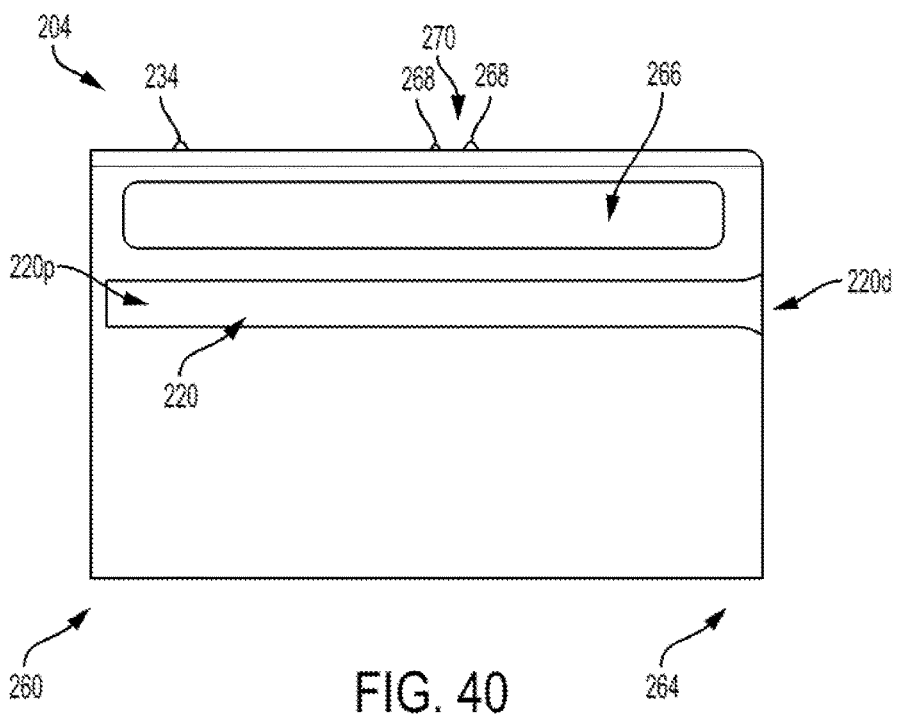
FIG. 40 is a side view of the inner member of FIG. 39.
Figure 41:
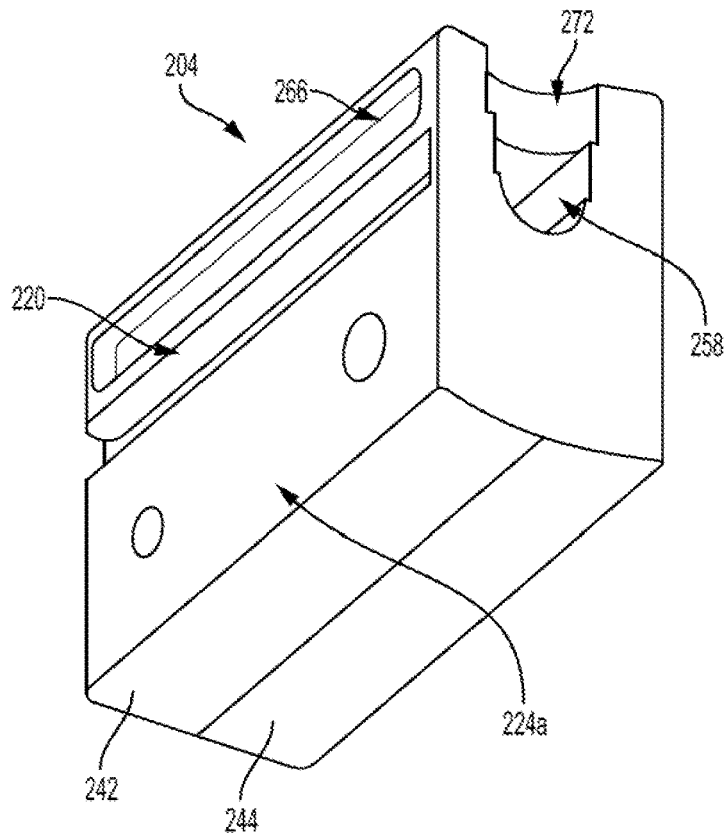
FIG. 41 is another perspective view of the inner member of FIG. 39.

FIGS. 30-35 illustrate one embodiment of a loading element 200 including a first loading member 202 and a second loading member 204. The "first loading member" is also referred to herein as an "outer housing" and an "outer member," and the "second loading member" is also referred to herein as an "inner housing" and an "inner member." The inner member 204 can be configured to be seated at least partially within the outer member 202, as shown in FIGS. 30-35. FIGS. 36-38 illustrate the outer member 202 as an independent element, and FIGS. 39-41 illustrate the inner member 204 as an independent element.

The loading element 200 can be configured to facilitate loading of a plate (not shown) into a surgical instrument (not shown) configured to pass a suture through tissue. The loader 200 can be configured to have the plate loaded therein for delivery of the plate to the surgical instrument. The plate can be pre-loaded therein, e.g., during manufacturing. The plate may thus be properly loaded into the loader 200 since it is loaded therein according to manufacturing specifications. Alternatively, the loader 200 may not have the plate pre-loaded therein, and the plate can be manually loaded into the loader 200 by a user. The user may thus select by preference a particular plate.

The loader 200 can be disposable. In other words, after the loader 200 is used to load the plate into a surgical instrument, the loader 200 can be disposed of according to applicable standards of discarding used medical devices or elements thereof. The loader 200 being disposable may limit improper loading of a retention plate therein, and hence improper delivery of the plate to a surgical instrument, since the loader 200 can be pre-loaded with a plate and disposed after the one loading of the one plate into a surgical instrument.

In general, as discussed further below, the outer member 202 can be configured to movably seat the inner member 204 therein, the inner member 204 can be configured to removably and replaceably seat a retainer plate therein, and the inner member 204 can be configured to receive a distal portion of a surgical instrument therein, such as at least a portion of an end effector of the instrument. Movement of one of the outer and inner housings 202, 204 relative to the other can be configured to cause the plate seated in the inner member 204 to move from being seated in the loader 200 (e.g., from being seated in the inner member 204) to being seated in the distal portion of the surgical instrument received by the inner housing 204. In other words, the plate can move from being seated in the loader 200 to being seated in the surgical instrument (e.g., seated in an upper jaw of an end effector of the instrument) in response to the movement of the inner housing 204 and/or the outer housing 202. This movement of the plate from the loader 200 to the end effector can be automatic such that the act of the housing movement automatically causes the plate to move from the loader 200 to the surgical instrument. The plate may thus be easily loaded into the surgical instrument using the loader 200. No loading accessories other than the single loader 200 may be needed to accomplish the loading of the plate into the surgical instrument, thereby reducing equipment costs and/or resulting in a simple plate-loading procedure. The loader 200 can be configured such that, when the outer housing 202 is held in position (by hand and/or by tool) distal movement of the instrument received by the inner housing 204 can move the inner housing 204 distally within the outer housing 202.

Figure 33:
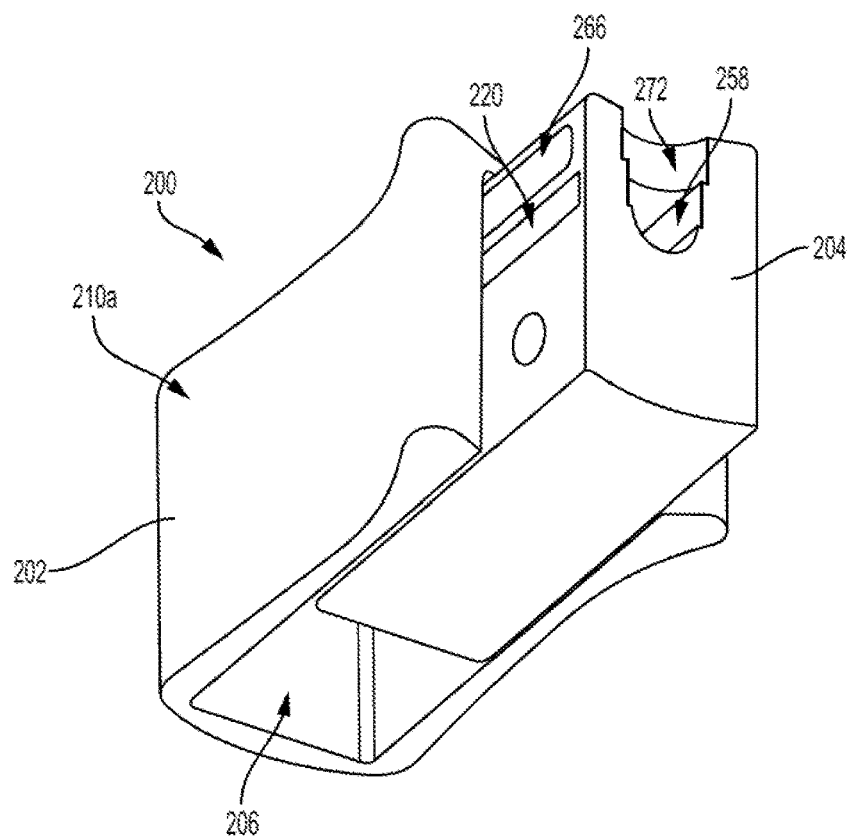
FIG. 33 is yet another perspective view of the loading element of FIG. 30.
Figure 34:
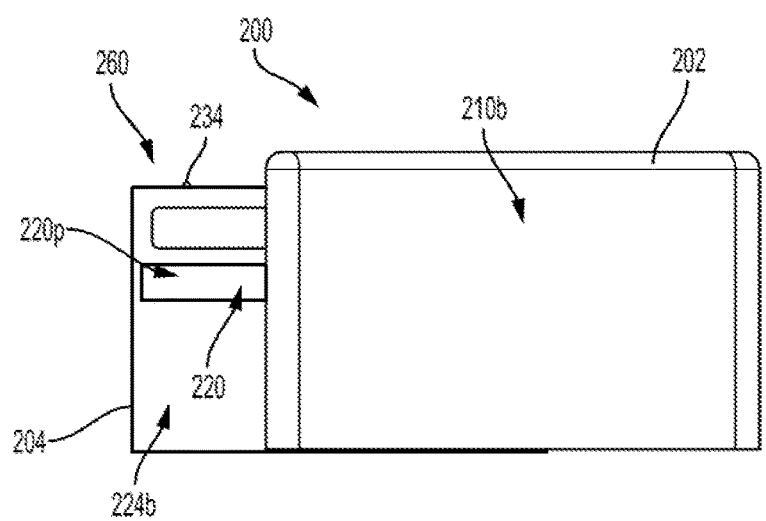
FIG. 34 is a side view of the loading element of FIG. 30.

The outer member 202 can have a variety of sizes, shapes, and configurations. The outer member 202 can include an internal cavity 206 therein. The internal cavity 206 can be defined by a top or upper side 208 of the outer member 202, by opposed lateral sides 210a, 210b of the outer member 202, and by a back or distal side 212 of the outer member 202. The outer member 202 can have an opening 214 at a proximal end 216 thereof that provides access to the internal cavity 206. The outer member 202 can have an open bottom or lower side. The bottom side being open may allow for visualization of the inner member 204 seated within the outer housing 202, as shown in FIG. 33. This visualization may help a user determine how much of the inner member 204 is disposed within the outer member 202, e.g., within the internal cavity 206 thereof. In other words, this visualization may help a user determine how far distally the inner member 204 has been advanced into the cavity 206.

The outer member 202 can be configured to receive the inner member 204 therein, e.g., within the inner cavity 206, in a single predetermined orientation relative thereto. The outer member 202 can include an engagement member 218 configured to cooperate with a corresponding engagement member 220 of the inner member 204, which is discussed further below, to orient the outer and inner members 202, 204 in a predetermined orientation with one another. The corresponding engagement members 218, 220 can thus be configured to prevent the inner housing 204 from being inserted into the inner cavity 206 of the outer housing 202 in any orientation other than the single predetermined orientation. The inner member 204 being receivable in the outer member 202 in only one predetermined orientation may prevent the inner member 204 from being inserted into the inner cavity 206 in an orientation relative to the outer member 204 in which the plate seated in the inner member 204 cannot be properly loaded into a surgical instrument mated to the loader 200. In other words, the inner member 204 being receivable in the outer member 202 in only one predetermined orientation may ensure that the outer and inner members 202, 204 are mated together in a relationship with each other to allow proper loading of the plate into the instrument.

The outer member's engagement member 218 can be configured to facilitate engagement of the outer member 202 with the inner member 204. The engagement member 218 can have a variety of sizes, shapes, and configurations. As shown in FIGS. 36-38, the outer member's engagement member 218 can include one or more rails extending longitudinally along an interior surface 222a, 222b of the outer member 202, with a first interior surface 222a being on one lateral side 210a of the outer housing 202 and a second interior surface 222b being on the other lateral side 210b of the outer housing 202. The outer member 202 includes four rails in this illustrated embodiment (one of the rails on one side 210a of the outer member 202 is obscured in FIGS. 36-38 but is visible in FIG. 44, which is discussed further below) but can include another number, e.g., one, two, three, five, etc. As discussed further below, the inner member's engagement member 220 in this illustrated embodiment includes one or more tracks extending longitudinally along an exterior surface 224a, 224b of the inner member 204 that can be configured to slidably engage the one or more rails 218, with a first exterior surface 224a being on one lateral side of the inner housing 204 and a second exterior surface 224b being on another, opposite lateral side of the inner housing 204. Alternatively, the outer member's engagement member can include one or more tracks, and the inner member's engagement member can include one or more rails configured to slidably engage the one or more tracks.

The outer member 202 can include a boss 226 (see FIGS. 31 and 44) configured to urge a plate seated in the inner member 202 out of the inner member 204 (and hence out of the loader 200) and into the surgical instrument received by the inner member 204. The boss 226 can extend downwardly from an interior surface 228 of the top side 208 of the outer member 202. In this illustrated embodiment, the boss 226 includes a longitudinally extending tab. The boss 226 can be located distal to a proximal-most end 230 of the outer member's engagement member 218, thereby allowing the engagement members 218, 220 to be engaged before the boss 226 begins urging the plate out of the inner member 204. The outer and inner members 202, 204 may thus be properly oriented relative to one another before the plate begins moving out of the loader 200 and into the surgical instrument such that the plate may be properly loaded into the instrument without being misaligned relative to the instrument and/or becoming deformed during the loading process.

The outer member 202 can include one or more protrusions 232 configured to facilitate confirmation of complete advancement, e.g., full distal movement, of the inner member 202 into the internal cavity 206 of the outer member 202. A plate seated in the inner member 204 when the inner member 204 has been fully advanced out of the inner member 204 before the inner member 204 has been completely advanced into the outer member 202. The confirmation of the inner member's complete advancement into the outer member 202 thus confirms that the plate has been fully advanced out of the loader 200 and has been fully advanced into the surgical instrument. As discussed further below, the one or more protrusions 232 can be configured to cooperate with one or more ribs 234 of the inner member 204 to facilitate the confirmation of complete advancement of the inner member 204 into the internal cavity 206 of the outer member 202 by providing audible confirmation thereof. In general, the one or more protrusions 232 engaging the one or more ribs 234 can generate an audible sound and can be tactilely felt by a user using the loader 200. The confirmation of complete advancement can thus be audible and tactile. The outer member 202 includes two protrusions 232 in this illustrated embodiment (only one of the protrusions 232 is visible in FIG. 36 near one lateral side 210b, but a similar protrusion is located near the other lateral side 210a), but an outer member can include another number of protrusions (e.g., one, three, four, etc.). The one or more protrusions 232 extend downwardly from the interior surface 228 of the top side 208 of the outer member 202 near the outer member's proximal end 216 in this illustrated embodiment, but any of the outer member's internal surfaces can include any number of the one or more protrusions 232. The one or more protrusions 232 are spherical sections in this illustrated embodiment, but the one or more protrusions 232 can have another shape.

The outer member 202 can include one or more holes 238 formed in the top surface 208 thereof. The outer member 202 includes four holes 238 in this illustrated embodiment, but an outer member can include another number of holes (e.g., one, two, three, five, etc.). The one or more holes 238 are longitudinally extending rectangles in this illustrated embodiment, but an outer member can include hole(s) in different orientations and/or having different shapes. As shown in FIG. 35, the one or more holes 238 can be configured to facilitate visualization of the inner member 204 within the inner cavity 206 of the outer member 202.

The outer member 202 can include a proximal cut-out 236 configured to facilitate visual confirmation of the inner member's complete advancement into the inner cavity 206 of the outer member 204 and, hence, complete advancement of the plate out of the loader 200 and into the surgical instrument. The cut-out 236 has a half-moon shape in this illustrated embodiment but can have another shape. By being located at the proximal end 216 of the outer member 202, a proximal end of the plate loaded into an instrument using the loader 200 can be visible therethrough. Thus, protrusions at proximal ends of opposed arms of the plate can be visible through the proximal cut-out. The plate's proper seating in the instrument may thus be visually verified, e.g., movement of the arms' protrusions into a proximal-most portion of a cavity formed in the instrument's upper jaw.

The outer member 202 can include one or more distal openings 240 (see FIG. 36) formed in the back or distal side 212 thereof. The outer member 202 includes one distal opening 240 in this illustrated embodiment, but an outer member can include another number of distal openings (e.g., two, three, four, etc.). The one or more distal openings 240 are circular in this illustrated embodiment, but an outer member can include distal opening(s) having another shape. The one or more distal openings 240 can be configured to facilitate removal of the inner member 204 from the internal cavity 206 of the outer member 202. When the inner member 204 is advanced into the outer member 202, there may not be enough (or any) of the inner member 204 extending proximally beyond the proximal end 216 of the outer member 202 so as to not provide enough (or any) proximal portion of the inner member 204 to be grasped for pulling of the inner member 204 out of the outer member's internal cavity 206. Similarly, when the inner member 204 is advanced into the outer member 202, there may not be enough (or any) space between distal ends of the outer and inner members 202, 204 such that a finger or a tool cannot be inserted therebetween through the open bottom side of the outer member 202 to push the inner member 204 out of the outer member's internal cavity 206. The one or more distal openings 240, being formed through the outer member's back side 212 can be accessible even when the inner member 204 is fully advanced into the outer member 202. A tool can be inserted into the one or more distal openings 240 and used to push the inner member 204 out of the outer member's internal cavity 206, either fully out or partially out before the inner member 204 is otherwise removed from the outer member 202 (e.g., pulling of the inner member 204 by hand). Even if the loader 200 is disposable such that the inner member 204 need not be removed from the outer member 202 for reuse, the inner member 204 may need to be removed from the outer member 202 during use for any number of reasons, such as a desire to load a different plate into the loader 200, a desire to clean the loader 200 of fluid and/or other matter, etc.

Figure 42:
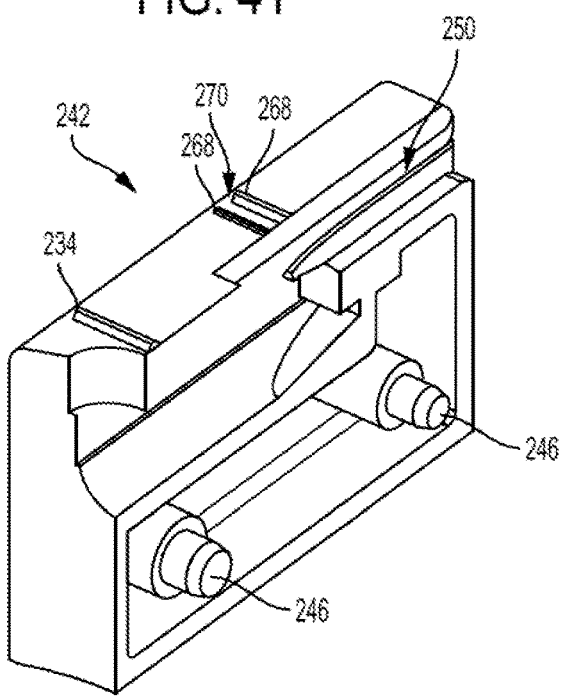
FIG. 42 is a perspective view of a first lateral half of the inner member of FIG. 39.
Figure 43:
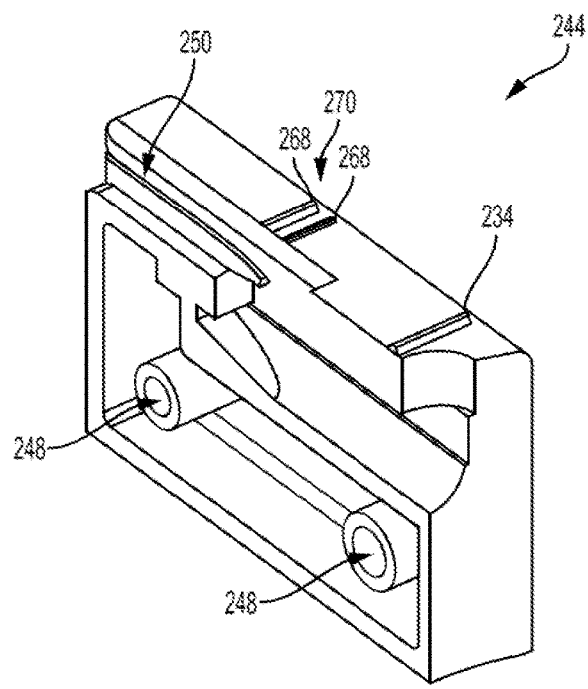
FIG. 43 is a perspective view of a second lateral half of the inner member of FIG. 39.

The inner member 204 can have a variety of sizes, shapes, and configurations. As shown in FIGS. 39, 42, and 43, the inner member 204 can include first and second halves 242, 244 that can be coupled together to form the inner member 204. The inner member 204 being two pieces may facilitate manufacturing of the inner member 204. In other embodiments, an inner member can be a single piece or can include more than two pieces that together form the inner member. One of the inner member's halves 242 can include one or more pegs 246 configured to be received in one or more corresponding holes 248 formed in the other half 244 to facilitate assembly of the inner member 204. Each of the pegs 246 can have a different size, e.g., a different diameter. Each of the holes 248 can also have a different size, e.g., a different diameter. The differently sizes pegs 246 and holes 248 may prevent the inner member 204 from being assembled in any way other than one. In other words, the halves 242, 244 can be configured to be coupled together in only one predetermined orientation relative to one another. The inner member 204 may thus be properly assembled.

The inner member 204 can include a proximal bore 258 formed therein. The bore 258 can be formed in a proximal portion of the inner member 204, e.g., formed through a proximal end 260 of the inner member 204. The bore 258 can be configured to receive at least a distal portion of an end effector of a surgical instrument therein. The bore 258 can thus have a size and shape configured to facilitate introduction of at least a portion of an instrument's end effector therein. The bore 258 can be configured to receive the end effector therein in only one predetermined orientation relative to the inner member 204. The end effector (e.g., an upper jaw thereof) may thus be properly positioned relative to the plate loaded in the inner member 204 for delivery of the plate from the loader 200 to the end effector.

The bore 258 can have a cross-sectional shape configured to receive the end effector therein in only the one predetermined orientation. End effectors of surgical instruments configured to facilitate passage of suture through tissue traditionally have a "D" cross-sectional shape when closed. Thus, as shown in FIGS. 30, 33, 39, and 41, the bore 258 can have a D-shaped cross-section. Additionally, end effectors of surgical instruments configured to facilitate passage of suture through tissue traditionally have a smallest cross-sectional shape when closed, e.g., when jaws of the end effector are closed. The bore 258 can be sized such that the end effector being open has a size too large to be inserted into the bore 258. The bore 258 can thus be configured to receive an end effector therein only when the end effector is closed. The end effector (e.g., an upper jaw thereof) may thus be further ensured to be properly positioned relative to the plate loaded in the inner member 204 for delivery of the plate from the loader 200 to the end effector.

Figure 44:
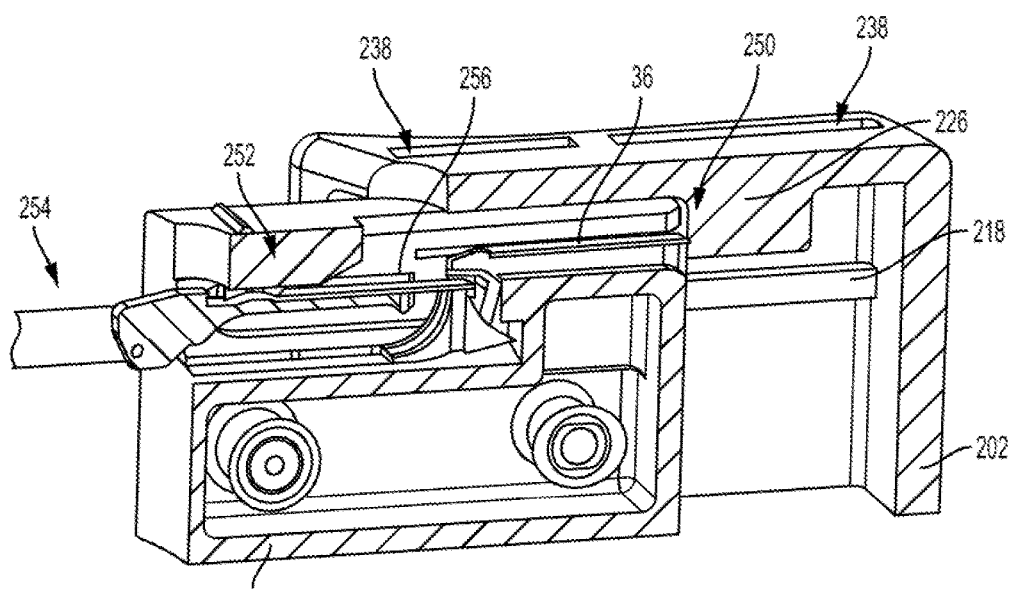
FIG. 44 is a perspective cross-sectional view of the loading element of FIG. 30 having the plate of FIG. 3 loaded therein and having loaded therein a distal portion of an end effector of another embodiment of a surgical instrument configured to pass a suture through tissue.

The inner member 204 can include a seat 250, illustrated in FIGS. 42-44, configured to removably and replaceably seat a retainer plate 36 prior to loading of the plate 36 into a surgical instrument 254 disposed within the bore 258. The plate 36 is in a loading configuration in such a position seated on the seat 250 prior to beginning its movement into the instrument 254. The plate 36 of FIG. 3 is shown seated in the seat 250 in FIG. 44 and is discussed below with respect to the loader 200 for ease of explanation, but the seat 250 can seat other types of plates, e.g., a plate similar to the plate 36 but formed from a different material, the plate 48 of FIG. 5, etc. Similarly, although FIG. 44 shows a portion of an end effector 252 of the surgical instrument 254 received in the inner member 204 for delivery of the plate 36 thereto, other instruments can be received in the inner member 204, e.g., the instrument 10 of FIG. 1, the instrument 80 of FIG. 8, etc., for delivery of the plate 36 (or other plate) thereto.

The seat 250 can include an elongate, longitudinally-extending channel formed in an interior of the inner member 204. The seat 250 can have a size and shape that generally corresponds to a size and shape of the plate 36 to be seated thereon 250.

The seat 250 can be located in a distal portion of the inner member 204. In this way, as the inner member 204 is advanced distally within the outer member's inner cavity 206 such that the inner member 204 is becoming closer to the outer member's distal side 212, the plate 36 can be urged out of the inner member 204 by the boss 226 and into the end effector 252, e.g., into an upper jaw 256 of the end effector 252. The plate 36 can be configured to remain at a substantially fixed axial position relative to the outer member 202 during the inner member's distal advancement, e.g., at a substantially fixed position along a longitudinal axis A6 of the outer member 204 (see FIGS. 35 and 37). A person skilled in the art will appreciate that the position may not be precisely fixed axially but nevertheless be considered to be substantially fixed axially due to, e.g., manufacturing tolerances, a texture thereon, and/or tolerances in measurement devices. The boss 226 can be configured to hold the plate 36 in the substantially fixed axial position during the inner member's distal advancement, thereby allowing the plate 36 to move from the seat 250 of the inner member 204 to the end effector 252 (e.g., the upper jaw 256 thereof) since the end effector 252 is advancing distally with the inner member 204.

The inner member 20 can include a longitudinal slot 262 formed in a top or upper side 264 thereof. The slot 262 can be in communication with the seat 250. The slot 262 can be configured to slidably receive the boss 226 therein. The boss 226 can therefore be configured to slide within the slot 262 and engage the plate 36 seated in the seat 250 to urge the plate 36 into the end effector 252. The slot 262 can extend from a distal end 264 of the inner member 204 to a position proximal to the inner member's proximal end 260. The slot 262 can thus have an open distal end and a closed proximal end. The slot's distal end being open may facilitate entry of the boss 226 into the slot 262. The slot's proximal end being closed may facilitate the stoppage of movement of the inner member 204 within the inner cavity 206 of the outer member 202, which may help prevent damaging the loader 200, the plate 37, and/or the instrument 254.

As mentioned above, the inner member 204 can include an engagement member 220 configured to cooperate with the outer member's engagement member 218 to facilitate orientation of the inner member 204 relative to the outer member 202. The engagement member 220 can have a variety of sizes, shapes, and configurations. As mentioned above, the engagement member 220 in this illustrated embodiment includes one or more tracks extending longitudinally along the exterior surface 224a, 224b of the inner member 204 but can have other configurations. The inner member 204 includes two tracks 220 to correspond to the outer member's two rails 218 but in other embodiments can have another number of tracks.

Each of the tracks 220 can have an open distal end 220d and a closed proximal end 220p. The open distal ends 220d may facilitate entry of the rails 218 into the tracks 220. The closed proximal ends 220p may facilitate the stoppage of movement of the inner member 204 within the inner cavity 206 of the outer member 202. If the outer member's engagement member includes one or more tracks and the inner member's engagement member includes one or more rails, each of the tracks can have an open proximal end and a closed distal end, which may similarly facilitate the stoppage of movement of the inner member 204 within the inner cavity 206 of the outer member 202.

In this illustrated embodiment, the inner member 204 includes a hollowed space 266 on each its opposed lateral sides 224a, 224b. The hollowed spaces 266 may allow less material to be needed to form the inner member 204 and/or to otherwise facilitate manufacturing of the inner member 204.

As mentioned above, the inner member 204 can include one or more ribs 234 configured to cooperate with the outer member's one or more protrusions 232 to facilitate the confirmation of complete advancement of the inner member 204 into the internal cavity 206 of the outer member 202. The inner member 204 includes a single rib 234 in this illustrated embodiment. The one or more ribs 234 are located near the inner member's distal end 260 in this illustrated embodiment to cooperate with the one or more protrusions 232. In this way, the confirmation of complete advancement (e.g., the audible and/or tactile confirmation) may be produced when the inner member's distal end 260 approaches the outer member's proximal end 216.

The inner member 204 can include one or more ribs 268 located proximally to the one or more ribs 234 configured to cooperate with the outer member's one or more protrusions 232 to facilitate the confirmation of complete advancement of the inner member 204 into the internal cavity 206 of the outer member 202. For ease of discussion, the one or more ribs 234 near the inner member's proximal end 260 are referred to herein as "proximal ribs," and the one or more ribs 268 located distally to the one or more proximal ribs 234 are referred to herein as "distal ribs." The one or more distal ribs 234 can be configured to limit proximal movement of the inner member 204 relative to the outer member 202 after at least one of the distal ribs 234 has moved distally past one or more distal protrusions (not shown) of the outer member 204 that are located distal to the one or more protrusions 232. In order for the inner member 204 to move proximally, e.g., in a direction toward its exit from the inner cavity 206, the one or more distal ribs 234 and the outer member's one or more distal protrusions can be configured to cooperate to require that a threshold amount of force be applied to at least one of the outer and inner members 202, 204 to allow proximal movement of the inner member 204 relative to the outer member 202. The one or more distal ribs 234 and the outer member's one or more distal protrusions can thus be configured to cooperate to help prevent accidental back-out of the inner member 204 from the outer member 202.

In this illustrated embodiment, the inner member 204 includes two distal ribs 268. The two distal ribs 268 can define a trough 270 therebetween. The outer member's one or more distal protrusions can be configured to settle within the trough 270 after one of the distal ribs 268 passes distally beyond the outer member's one or more distal protrusions. The settling in the trough 270 may help hold the outer and inner members 202, 204 in a fixed position relative to one another until the predetermined amount of force is applied to at least one of the outer and inner members 202, 204 to allow proximal movement of the inner member 204 relative to the outer member 202. The more distal of the two distal ribs 268 can have a higher profile, e.g., a greater height, than the more proximal of the two distal ribs 268, as shown in FIGS. 40, 42, 44. This higher profile may facilitate settling of the outer member's one or more distal protrusions in the trough 270, as opposed to passing distally passed the more distal of the two distal ribs 268. Instead of including two distal ribs 268, an inner member can include one distal rib, three distal ribs (so as to define three troughs), etc.

The inner member 204 can include a proximal cut-out 272 configured to facilitate visual confirmation of the inner member's complete advancement into the inner cavity 206 of the outer member 204 and, hence, complete advancement of the plate out of the loader 200 and into the surgical instrument. The inner member's proximal cut-out 272 can generally be configured and used similar to the outer member's proximal cut-out 236, e.g., have a half-moon shape, facilitate visualization of the plate 36 seated in the upper jaw 256, etc.

As mentioned above, a surgical instrument configured to pass a suture through tissue and having a retainer plate loaded therein (e.g., loaded during manufacturing, loaded by hand, or loaded using any of the loading elements described herein) can be used in any of a variety of surgical procedures. FIGS. 46-56 illustrate one embodiment of a surgical procedure that can be performed using a surgical instrument 300, also shown in FIG. 45, having the plate 36 of FIG. 3 loaded therein. The procedure is illustrated with respect to the instrument 300 and the plate 36 but can be similarly performed using a different surgical instrument and/or a different plate. The instrument 300 can generally be configured and used similar to the instrument 10 of FIG. 1 and other surgical instruments described herein, e.g., include an elongate shaft 302 having the end effector 304 at a distal end thereof, be configured to removably and replaceably seat a needle 306 (see FIG. 51), include a handle portion 308 (see FIGS. 49-53), etc. The instrument 300 is shown with the plate 36 of FIG. 3 loaded therein, but the instrument 300 can be used with this plate 36 and/or other plates, e.g., a plate similar to the plate 36 but formed from a different material, the plate 48 of FIG. 5, the plate 72 of FIG. 7, etc. The instrument's end effector 304 can generally be configured and used similar to the end effector 16 of FIG. 1 and other end effectors described herein, e.g., include upper and lower jaws 310a, 310b, be movable between open and closed positions, etc. In this illustrated embodiment, the end effector 304 includes upper and lower jaws 310a, 310b, with the upper jaw 310a being configured to move relative to the lower jaw 310b and the elongate shaft 302. The upper jaw 310a can generally be configured and used similar to the upper jaw 86a of FIG. 8 and other upper jaws described herein. In this illustrated embodiment, the upper jaw 310a has a gap 312 formed therein (e.g., has a non-continuous upper rim 313), has a non-linear interior surface 314, includes a pair of retention tabs 316a, 316b, has a cavity 318 formed in an upper side thereof that includes a distal portion, a tapered proximal portion, and a proximal-most portion, etc.

Figure 45:
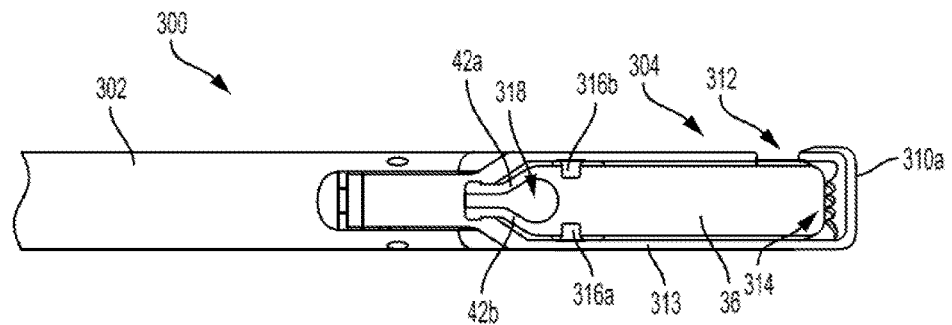
FIG. 45 is a top view of a distal portion of another embodiment of a surgical instrument configured to pass a suture through tissue, the instrument having the plate of FIG. 3 loaded in an end effector thereof.
Figure 46:
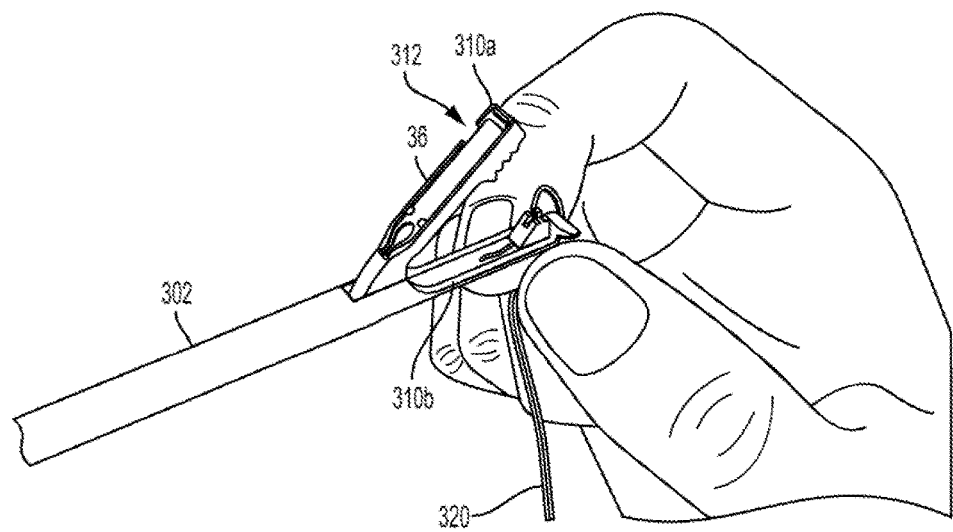
FIG. 46 is a perspective view of a suture being loaded by hand into the end effector of FIG. 45.
Figure 47:
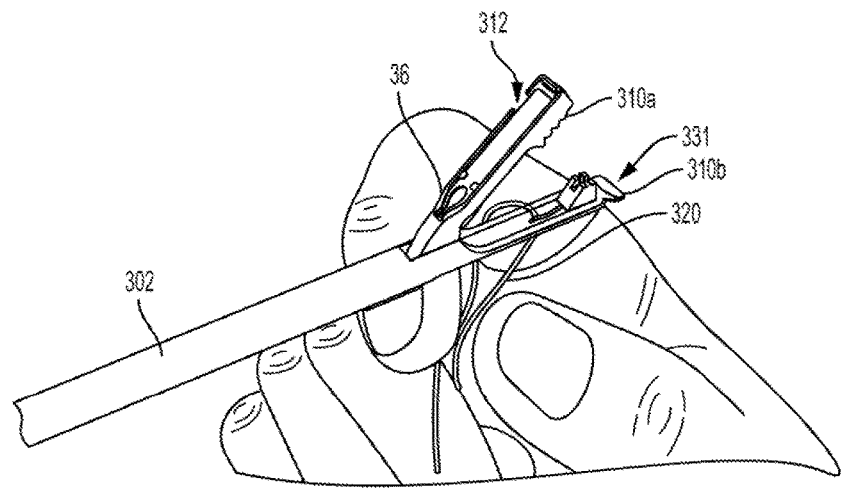
FIG. 47 is a perspective view of the suture of FIG. 46 continuing to be loaded by hand into the end effector of FIG. 46.
Figure 48:
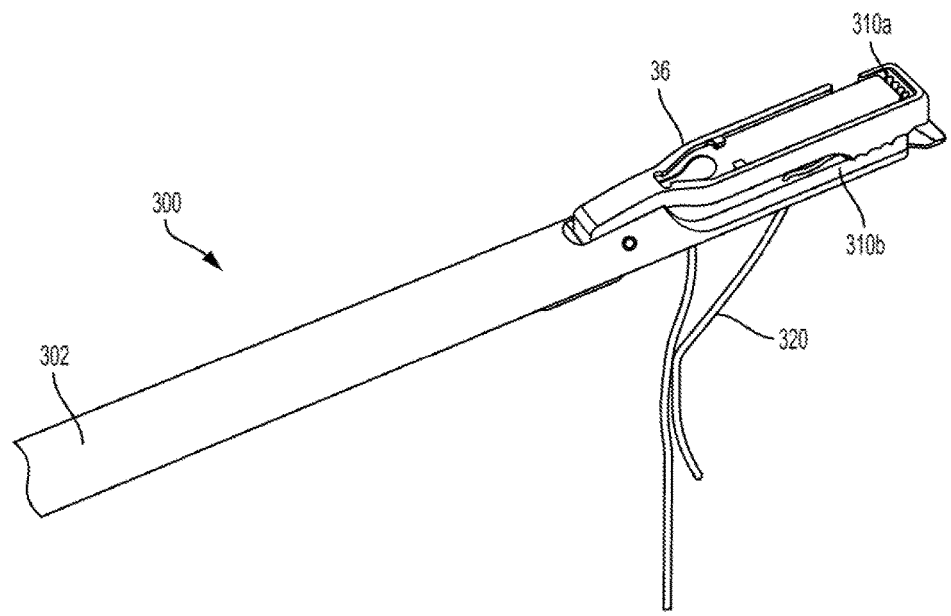
FIG. 48 is a perspective view of the suture of FIG. 47 loaded into the end effector of FIG. 47.

FIG. 45 illustrates the plate 36 properly loaded in the upper jaw 310a, with the arms 42a, 42b of the plate 36 locked in position within the cavity 318, e.g., with the arms' protrusions 43a, 43b locked within the cavity's proximal-most portion. After the plate 36 is loaded into the instrument 300, the needle 306 can be loaded into the instrument 300. Embodiments of needle loading are further described in previously mentioned U.S. Pat. No. 8,540,732 entitled "Suturing Apparatus And Method" filed Dec. 17, 2010. Alternatively, the needle 306 can be loaded into the instrument 300 before the plate 36 is loaded therein. After the plate 36 and the needle 306 are loaded into the instrument 300, a suture 320 can be loaded into the end effector 304, e.g., into the bottom jaw 310b. FIGS. 46-48 illustrate loading of the suture 320 into the end effector 304, e.g., into the bottom jaw 310b. Alternatively, the suture 320 can be loaded into the end effector 304 before the plate 36 and/or before the needle 306. Embodiments of suture loading are further described in previously mentioned U.S. Pat. No. 8,540,732 entitled "Suturing Apparatus And Method" filed Dec. 17, 2010.

Figure 49:
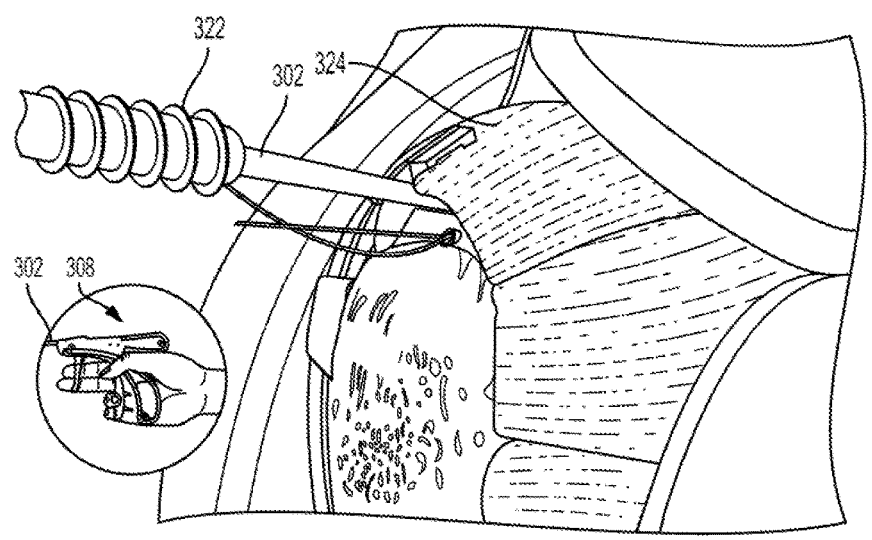
FIG. 49 is a perspective view of a distal portion of the surgical instrument of FIG. 48 inserted into a body of a patient with jaws of the end effector open around a rotator cuff tissue, an insert showing a proximal portion of the instrument being held by hand.
Figure 50:
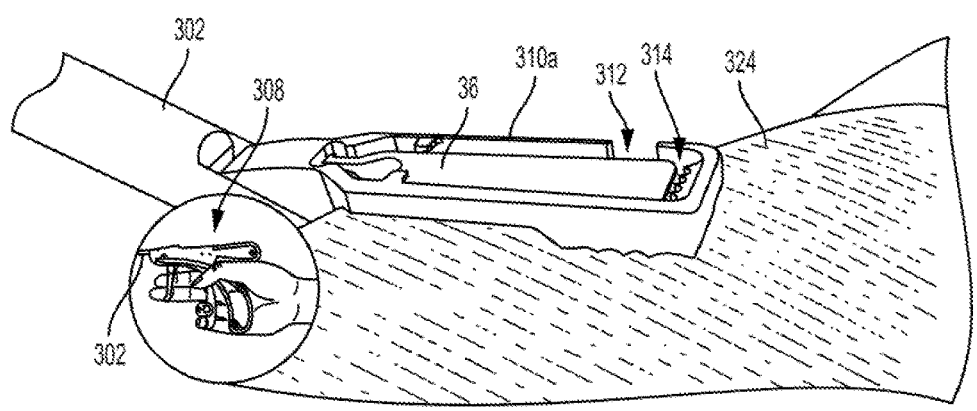
FIG. 50 is a perspective view of the jaws of the end effector of FIG. 49 clamped on the rotator cuff tissue, an insert showing the proximal portion of the surgical instrument being held by hand.
Figure 51:
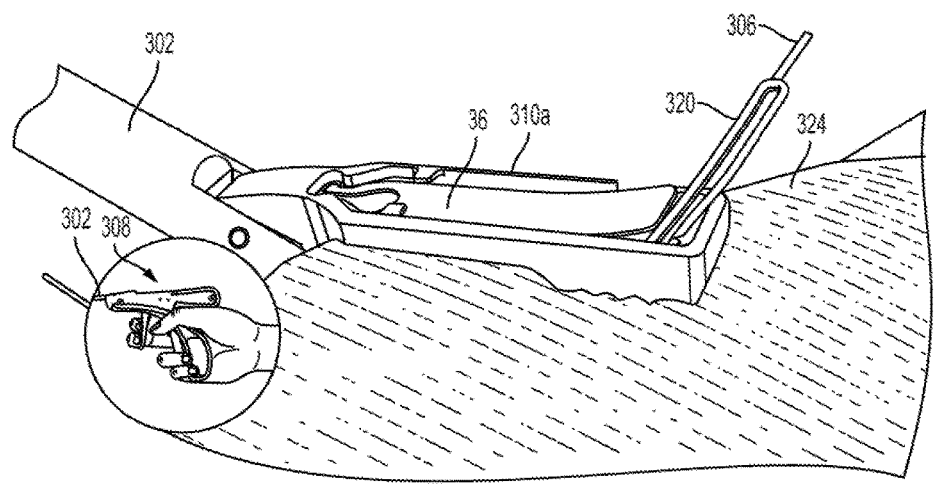
FIG. 51 is a perspective view of a needle and the suture of FIG. 48 advanced through the rotator cuff tissue of FIG. 50 clamped by the jaw of the end effector.

With the plate 36, the needle 306, and the suture 320 loaded, a distal portion of the instrument 300 including the end effector 304 can be advanced into a body of a patient, such as through a cannula 322, as shown in FIG. 47. The end effector 304 within the body can engage and bite a tissue 324, as shown in FIGS. 47 and 48, such that the tissue 324 is clamped between the jaws 310a, 310b. The tissue 324 in this illustrated embodiment includes a rotator cuff tissue. With the tissue 324 clamped by the end effector 304, as shown in FIG. 49, the needle 306 can be moved relative to the shaft 302 and the end effector 304 so as to advance out of the end effector 304 and through the tissue 324. The advancement of the needle 306 can cause a distal portion of the plate 36 to deform in an upward direction, as shown between the plate's undeflected position in FIGS. 45-50 and the plate's deflected position in FIG. 51. The advancement of the needle 306 can also cause the suture 320 to advance out of the end effector 304, as shown in FIG. 51. The portion of the suture 320 advanced out of the end effector 304 can include the loop previously loaded into the bottom jaw 310b, as shown. The needle 306 can then be retracted, as shown in FIG. 52, leaving the suture 320 (e.g., a loop thereof) outside of the end effector 304.

Figure 52:
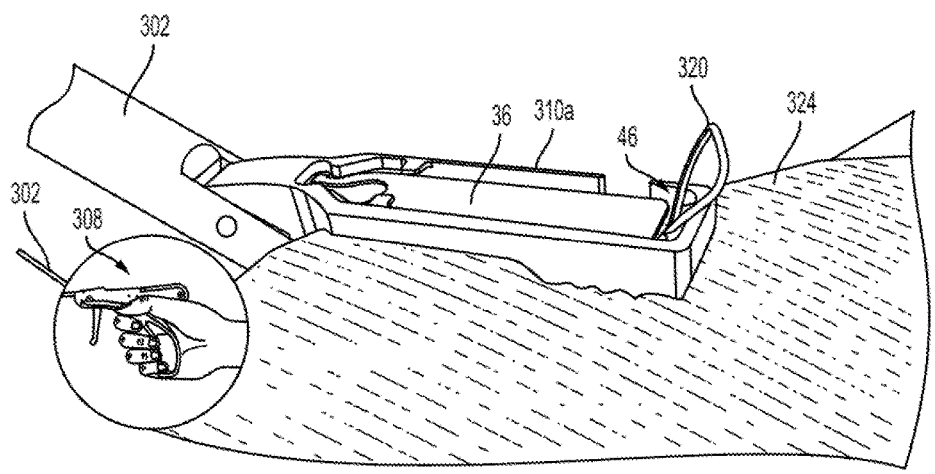
FIG. 52 is a perspective view of the suture of FIG. 51 advanced through the rotator cuff tissue clamped by the jaw of the end effector, the needle having been retracted.

The retraction of the needle 306 can allow the plate 36 to move from the deflected position toward the undeflected position, as shown between the plate's deflected position in FIG. 51 and the plate's partially deflected position in FIG. 52. In other words, the plate 36 can deform back toward the undeflected position. The plate 36 may not reach its undeflected position and instead be partially deflected, as in this illustrated embodiment, due to any one or more factors, such as the plate's deformable nature, the size of the suture 320, the force with which the needle 306 is advanced out of the end effector 304, etc. As also shown in FIG. 52, the suture 324 can be positioned between the distal-most surface 46 of the plate 36 and the non-linear interior surface 314 of the upper jaw 310a. As discussed above, the plate's distal-most surface 46 and the upper jaw's non-linear interior surface 314 can cooperate to help the instrument 300 (e.g., the upper jaw 310a) have a secure hold on the suture 320.

Figure 53:
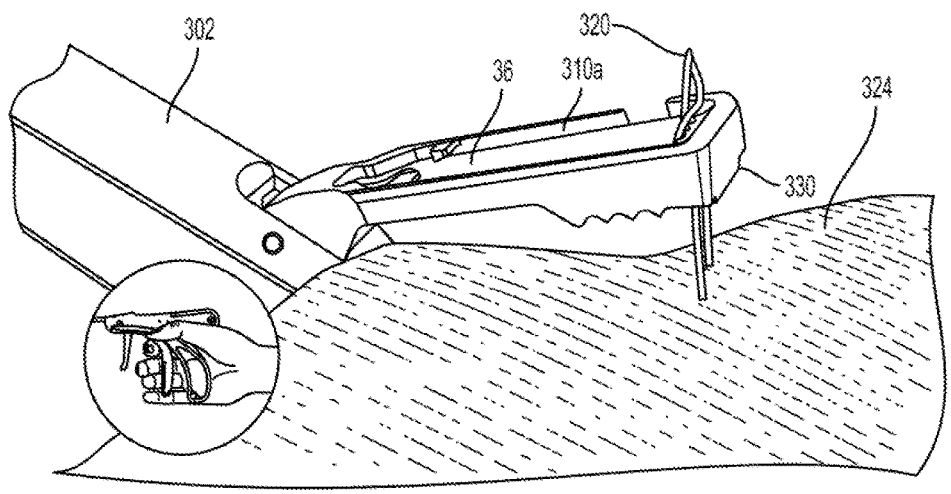
FIG. 53 is a perspective view of the jaws of the end effector of FIG. 52 opened with the suture passed through the tissue held by the jaws of the end effector.
Figure 54:
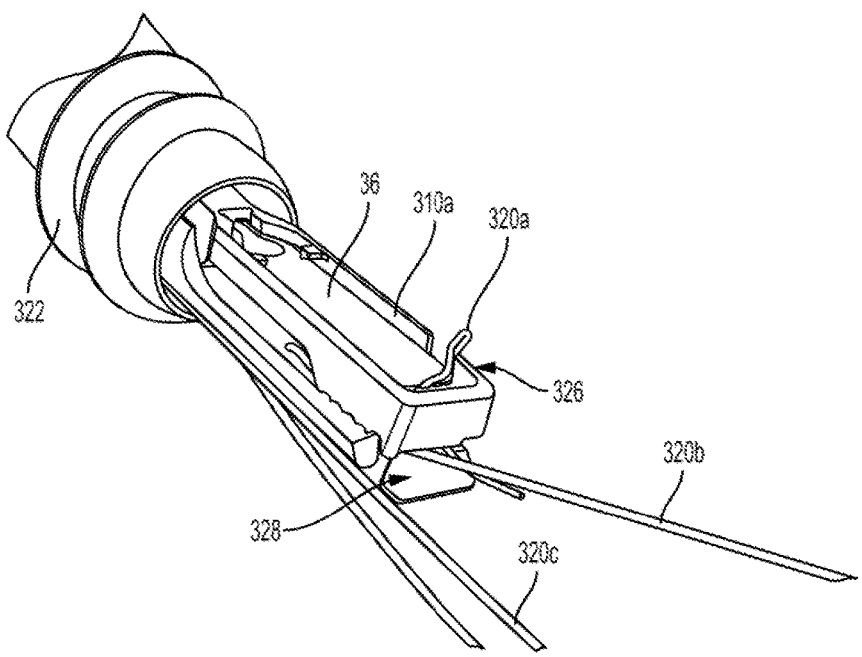
FIG. 54 is a perspective view of the jaws of the end effector of FIG. 53 closed with the suture passed through the tissue held by the jaws of the end effector.

After the retraction of the needle 320, the end effector 304 can be opened, as shown in FIG. 53. The suture 320 remains passed through the tissue 324 and remains held by the instrument 300 (e.g., by the upper jaw 310a). The instrument 300 can then be removed from the patient's body, e.g., by being retracted through the cannula 322. The end effector 304 can be moved from the open position to the closed position, as shown in FIG. 54, to facilitate removal of the end effector 304 from the patient's body since the end effector 304 has a smaller profile in the closed position than in the open position. Since the suture 320 is held by the instrument 300, the instrument's removal from the patient's body draws the suture 320 therewith. In other words, pulling the instrument 300 out of the patient's body causes the suture 320 to be pulled out of the patient's body, with a portion of the suture 320 remaining passed through the tissue 324. As shown in FIG. 54, a first portion 320a of the suture 320 (e.g., the loop of suture 320) can be held by the upper jaw 310a, a second portion 320b of the suture 320 extending from the first portion 320a can extend toward the tissue 324 (not shown in FIG. 54), a third portion (not shown in FIG. 54) of the suture 320 extending from the second portion 320b can be positioned within the tissue 324, and a fourth portion 320c of the suture 320 extending from the third portion of the suture 320 can extend through the cannula 322 and outside the patient's body. FIG. 54 also illustrates a primary capture point 326 of the suture 320 by the instrument 300 in the upper jaw 310a between the plate 36 (e.g., the plate's distal-most surface 46) and the upper jaw's non-linear interior surface 314, and a secondary capture point 328 of the suture 320 by the instrument 300 between the upper and lower jaws 310a, 310b, e.g., between a bucktooth 330 (see FIG. 53) of the upper jaw 310a and a suture-engaging surface 331 (see FIG. 47) of the bottom jaw 310b.

Figure 55:
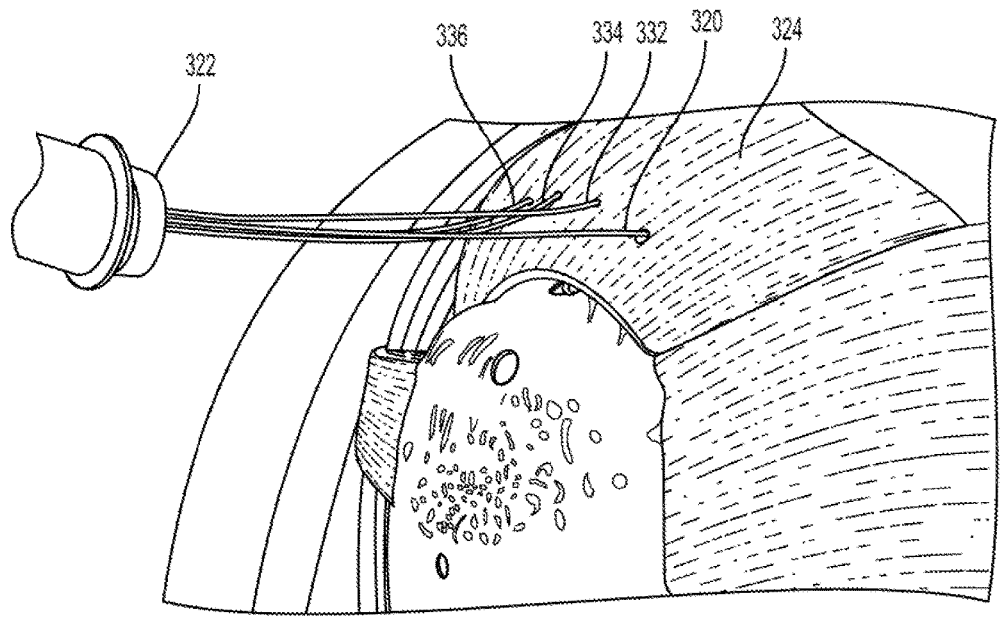
FIG. 55 is a perspective view of the suture of FIG. 54 passed through the rotator cuff tissue and a plurality of additional sutures passed through the rotator cuff tissue.
Figure 56:
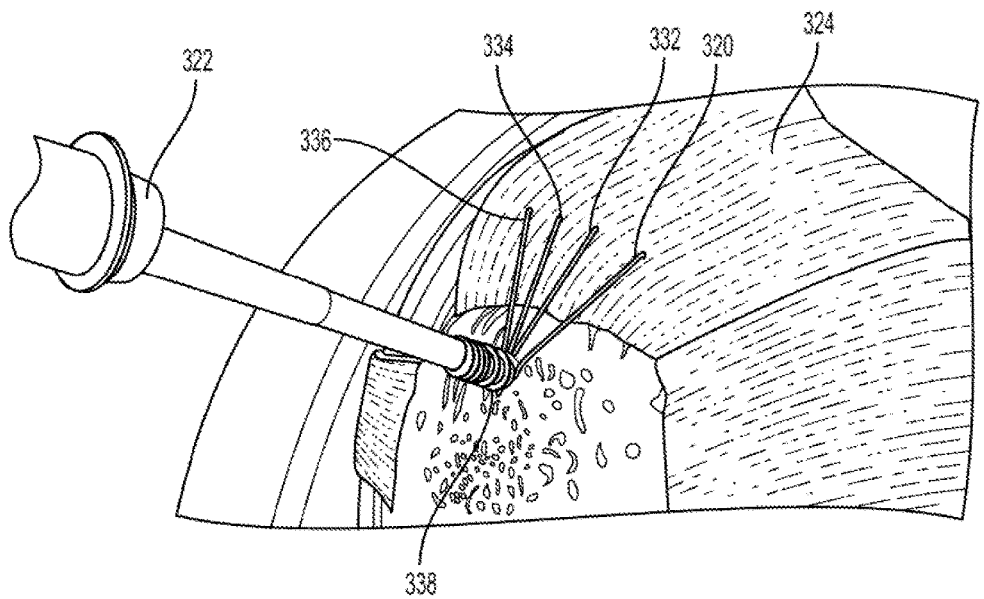
FIG. 56 is a perspective view of a suture anchor anchoring the sutures of FIG. 55.

After the instrument 300 has been removed from the patient's body through the cannula 322, the suture 320 can be disengaged (e.g., by hand) from the instrument 300, such as by being slid through the gap 312. One or more additional sutures can be sequentially loaded onto the instrument 300 and passed through the tissue 324, as shown in FIG. 55. A total of four sutures 320, 332, 334, 336 are passed through the tissue 324 in this illustrated embodiment, but any number of sutures can be passed through the tissue 324. As shown in FIG. 56, the sutures 320, 332, 334, 336 passed through the tissue 324 can then be used to tension the tissue 324 in position using a suture anchor 338 advanced into the patient's body through the cannula 322. Exemplary configurations of a suture anchor include the following anchors, all commercially available from DePuy Mitek of Raynham, Ma.: HEALIX®, HEALIX PEEK®, and HEALIX BR®, and include suture anchors described in U.S. Pat. No. 8,114,128 entitled "Cannulated Suture Anchor" issued Feb. 14, 2012, and U.S. Patent No. 2009/0076544 entitled "Dual Thread Cannulated Suture Anchor" filed Sep. 14, 2007, which are hereby incorporated by reference in their entirety.

A person skilled in the art will appreciate that the implementations described herein have application in conventional minimally-invasive and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components of the invention described herein will be processed before use. First, a new or used instrument is obtained and if necessary cleaned. The instrument can then be sterilized. This can be done by any number of ways known to those skilled in the art including beta or gamma radiation, ethylene oxide, steam, and a liquid bath (e.g., cold soak). In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical system, comprising:
   a surgical instrument including at a distal end thereof first and second jaws configured to grasp tissue therebetween, the surgical instrument being configured to pass a suture through tissue;
   a plate configured to facilitate manipulation of the suture; and
   a loading element including an outer housing and an inner housing that is configured to be seated at least partially within the outer housing, at least one of the inner and outer housings being movable relative to the other, the inner housing being configured to removably and replaceably seat the plate in a loading configuration, and the inner housing being configured to receive at least a portion of the first jaw therein;
   wherein when the inner housing is seated at least partially within the outer housing, the plate is seated in the inner housing, and at least the portion of the first jaw is received in the inner housing, movement of the outer housing relative to the inner housing is configured to cause the plate to move into the first jaw in a loaded configuration;
   wherein the inner housing has a bore formed therein that is configured to receive the portion of the first jaw therein; and
   the outer housing has an internal protrusion that extends into an internal cavity of the outer housing, the internal protrusion being configured to push the plate into the bore to cause the plate to move into the first jaw in the loaded configuration.

2. The system of claim 1, wherein the first and second jaws are configured to move between open and closed positions.

3. The system of claim 2, wherein the pair of jaws in the closed position define a first longitudinal axis;
   the bore formed in a proximal end of the inner housing is configured to receive the portion of the first jaw therein;
   the bore of the inner housing defines a second longitudinal axis; and
   the distal end of the surgical instrument is configured to be inserted into the bore with the first and second longitudinal axes being substantially parallel to one another.

4. The system of claim 1, wherein the surgical instrument includes an elongate shaft having the first and second jaws at a distal end thereof, the elongate shaft defining a first longitudinal axis; and
   the bore of the inner housing defines a second longitudinal axis, the bore being configured to receive at least the portion of the first jaw therein with the first and second longitudinal axes being substantially parallel to one another.

5. The system of claim 1, wherein the inner housing has a single position relative to the outer housing in which the inner housing is configured to be seated at least partially within the outer housing.

6. The system of claim 1, wherein the inner and outer housings have corresponding engagement members configured to orient the inner and outer housings relative to one another in a predetermined orientation.

7. The system of claim 6, wherein the engagement member of one of the inner and outer housings includes a slot, and the engagement member of the other of the inner and outer housings includes a protrusion configured to slide within the slot during the at least partial seating of the inner housing within the outer housing.

8. The system of claim 1, wherein the inner housing has a slot formed in an external surface thereof, the slot having an open proximal end and a closed distal end.

9. The system of claim 1, wherein the inner housing includes a stop element configured to stop movement of the inner housing in a distal direction within the outer housing once the inner housing has advanced a predetermined amount into the outer housing.

10. The system of claim 1, wherein in response to the plate being fully moved into the first jaw, at least one of the inner and outer housings is configured to generate at least one of an audible confirmation and a tactile confirmation of the plate being in the loaded configuration.

11. The system of claim 1, wherein the distal end of the surgical instrument is configured to be inserted into the bore formed in the inner housing, and the inner and outer housings are configured to cause the plate to move into the first jaw within the bore.

12. The system of claim 11, wherein the distal end of the surgical instrument is configured to be inserted into the bore of the inner housing in a single predetermined orientation relative to the inner housing.

13. A surgical system, comprising:
    a surgical instrument including at a distal end thereof first and second jaws configured to grasp tissue therebetween, the surgical instrument being configured to pass a suture through tissue;
    a plate configured to facilitate manipulation of the suture; and
    a loading element including an outer housing and an inner housing that is configured to be seated at least partially within the outer housing, at least one of the inner and outer housings being movable relative to the other, the inner housing being configured to removably and replaceably seat the plate in a loading configuration, and the inner housing being configured to receive at least a portion of the first jaw therein;

wherein when the inner housing is seated at least partially within the outer housing, the plate is seated in the inner housing, and at least the portion of the first jaw is received in the inner housing, movement of the outer housing relative to the inner housing is configured to cause the plate to move into the first jaw in a loaded configuration;

wherein the inner housing has one or more ribs formed on a top surface thereof;

wherein a distal end of the inner housing is configured to be inserted through an opening of the outer housing to be seated at least partially within the outer housing; and the one or more ribs are configured to at least one of prevent the inner housing from backing out of the outer housing in a proximal direction until a predetermined amount of force is applied to at least one of the inner and outer housings, and limit movement of the inner housing in the proximal direction relative to the outer housing and in a distal direction relative to the outer housing until a predetermined amount of force is applied to at least one of the inner and outer housings.

\* \* \* \* \*